(12) United States Patent
Perler et al.

(10) Patent No.: US 7,157,224 B2
(45) Date of Patent: Jan. 2, 2007

(54) SCREENING AND USE OF AGENTS WHICH BLOCK OR ACTIVATE INTEIN SPLICING UTILIZING NATURAL OR HOMOLOGOUS EXTEINS

(75) Inventors: Francine B. Perler, Brookline, MA (US); Eric E. Adam, Beverly, MA (US)

(73) Assignee: New England Biolabs, Inc., Ipswich, MA (US)

( * ) Notice: Subject to any disclaimer, the term of this patent is extended or adjusted under 35 U.S.C. 154(b) by 435 days.

(21) Appl. No.: 10/324,023

(22) Filed: Dec. 18, 2002

(65) Prior Publication Data

US 2003/0143522 A1    Jul. 31, 2003

Related U.S. Application Data

(60) Division of application No. 09/430,221, filed on Oct. 29, 1999, now Pat. No. 6,521,425, which is a continuation-in-part of application No. 08/811,492, filed on Mar. 5, 1997, now Pat. No. 5,834,247, which is a continuation-in-part of application No. 08/580,555, filed on Dec. 29, 1995, now abandoned, which is a continuation-in-part of application No. 08/496,247, filed on Jun. 28, 1995, now abandoned, which is a continuation-in-part of application No. 08/146,885, filed on Nov. 3, 1993, now abandoned, which is a continuation-in-part of application No. 08/004,139, filed on Dec. 9, 1992, now Pat. No. 5,496,714.

(51) Int. Cl.
  *C12N 9/50* (2006.01)
  *C12N 15/62* (2006.01)
  *C12N 15/74* (2006.01)
  *C12N 15/79* (2006.01)
  *C12Q 1/25* (2006.01)

(52) U.S. Cl. .................. 435/4; 435/69.7; 435/252.3; 435/320.1; 536/23.4

(58) Field of Classification Search ............. 435/4, 435/29, 69.7, 252.3, 320.1
See application file for complete search history.

(56) References Cited

U.S. PATENT DOCUMENTS 5,322,785 A * 6/1994 Comb et al. .............. 435/194

(Continued)

FOREIGN PATENT DOCUMENTS

FR    2 739 859    * 4/1997

OTHER PUBLICATIONS

Belfort, Annu. Rev. Genet. 24:363 (1990).

(Continued)

*Primary Examiner*—Nashaat T. Nashed
*Assistant Examiner*—William W. Moore
(74) *Attorney, Agent, or Firm*—Harriet M. Strimpel

(57) ABSTRACT

In accordance with the present invention, there are provided selection systems and methods for screening for agents that control splicing of inteins in their native host protein (extein) or in homologous exteins. Specifically, there are provided positive genetic selection systems for the screening of agents which inhibit or activate protein splicing which comprise: a host cell containing a chromosomal gene encoding either a drug-resistant form of a target enzyme or a wild-type target enzyme, and a plasmid-borne gene encoding either a drug-sensitive form of the target enzyme, which is dominantly cytotoxic upon interaction with the drug, or a dominantly cytotoxic form of the target enzyme. In these systems the plasmid-borne gene contains an intein, and the inhibition or activation of splicing of the dominant cytotoxic form of the target enzyme by a given reagent results in the survival or death of the host cell. More specifically, positive genetic selection systems which utilize the M. xenopi GyrA intein or M. tuberculosis DnaB helicase intein are provided. Similar reporter systems utilizing native or homologous exteins and systems utilizing controllable inteins are provided, as are methods of controlling in vivo expression of proteins by modulating protein splicing with inhibiting or activating agents, and methods of controlling the delivery of proteinaceous drugs in vivo by modulating protein splicing.

8 Claims, 20 Drawing Sheets

METHODS OF SELECTING FOR AGENTS THAT INHIBIT OR ACTIVATE PROTEIN SPLICING

A. Selection of agents that inhibit splicing of active inteins

| Scheme | Intein Minus Gene | Intein Plus Gene | Result of Selection |
|---|---|---|---|
| 1 | Resistant to drug | Dominantly sensitive | Agent that blocks splicing allows growth when drug present to drug |
| 2 | Wild type or non-toxic | Dominant lethal | Agent that blocks splicing allows growth |
| 3 | Conditionally essential product can be inactivated under defined conditions | Protein product is always expressed | Agent that blocks splicing results in cell death in the absence of the active intein minus product |

B. Selection of agents that activate splicing of inactive inteins

| Scheme | Intein Minus Gene | Intein Plus Gene | Result of Selection |
|---|---|---|---|
| 4 | Resistant to drug | Dominantly sensitive | Agent that activates splicing blocks growth when drug present to drug |
| 5 | Wild type or non-toxic | Dominant lethal | Agent that activates splicing blocks growth |
| 6 | Conditionally essential product can be inactivated under defined conditions | Protein product is always expressed | Agent that activates splicing results in cell growth in the absence of the active intein minus product |

U.S. PATENT DOCUMENTS

| | | | | |
|---|---|---|---|---|
| 5,352,778 | A * | 10/1994 | Comb et al. | 536/23.2 |
| 5,496,714 | A | 3/1996 | Comb et al. | 435/69.7 |
| 5,500,363 | A * | 3/1996 | Comb et al. | 435/194 |
| 5,795,731 | A | 8/1998 | Belfort | 435/32 |
| 5,834,247 | A | 11/1998 | Comb et al. | 435/69.7 |
| 5,834,285 | A * | 11/1998 | Comb et al. | 435/194 |
| 6,191,154 | B1 * | 2/2001 | Landreth et al. | 514/369 |
| 6,858,775 | B1 * | 2/2005 | Xu et al. | 800/278 |

OTHER PUBLICATIONS

Cech. Annu. Rev. Biochem. 59:543 (1990).
Hunter, et al., Genes. Dev. 3:2101 (1989).
Hirata, et al., J. Biol. Chem., 265:6726 (1990).
Kane, et al., Science, 250:651 (1990).
Davis, et al., J. Bact. 173:5653 (1991).
Davis, et al. Cell 71:201-210(1992)+C51.
Perler, et al. Nucl. Acids Res. 22:1125-1127 (1994).
Perler, et al. Proc. Natl. Acad. Sci. 89:5577 (1992).
Xu, et al., Cell 75:1371-1377 (1993).
Perler, Nucl. Acids Res. 25:1087-1093 (1997).
Dalgaard, et al., J. Comput. Biol. 4:193-214 (1997).
Pietrokovski, et al., Protein Sci. 7:64-71 (1998).
Perler, Nucleic Acids Res. 27:346-347 (1999).
Davis, et al., EMBO J. 13:699-703 (1994).
Smith, et al., Genome Res. 7:802-819 (1997).
Cole, et al., Nature 393:537-544 (1998).
Gu, et al., J. Biol. Chem. 268:7372-7381 (1993).
Xu, EMBO J. 13:5517-5522 (1994).
Xu, EMBO J. 15:5146-5153 (1996).
Telenti, J. Bacteriol. 179:6378-6382 (1997).
Chong J. Biol. Chem. 273:10567-10577 (1998).
Liu, FEBS Letters 408:311-314 (1997).
Nogami, Genetics 147:73-85 (1997).
Kawasaki, J. Biol. Chem., 272:15668-15674 (1997).
Derbyshire, Proc. Natl. Acad. Sci. 94:11466-11471 (1997).
Southworth, BioTechniques 27:110-121 (1999).
Hodges, et al., Nucleic Acids Res. 20:6153-6157 (1992).
Wu, Proc. Natl. Acad. Sci. 95:9226-9231 (1998).
Swanberg and Wang, J. Mol. Biol., 197:729-736 (1987).
Marszalek and Kaguni, J. Biol. Chem., 267:19334-19340 (1992.
Shrimankar, et la., J. Bacteriol. 174:7689-7696 (1992).
Lebowitz and McMacken, J. Biol. Chem. 261:4738-4748 (1986).
Lohman Mol. Microbiol. 6:5-14 (1992).
Bouvier and Oreglia C.R. Acad. Si. Hebd. Seances Acad. Si. D. 280:649-652 (1975).
Maurer and Wong, J. Bacteriol. 170:3682-3688 (1988).
Saluja and Godson, J. Bacteriol. 177:1104-1111 (1995).
Sclafani, et al., Mol. Gen. Genet. 182:112-118 (1981).
Colas, et al., Nature, 380:548-550 (1996).
Trave, et al. EMBO J. 14:4922-4931 (1995).
Sander, et al. Microbiology 144:589-591 (1998).
Klabunde, et al., Nature Struct. Biol. 5:31-36 (1998).
Pietrokovski, Protein Sci. 3:2340-2350 (1994).
Duan, et al., Cell 89:555-564 (1997).
Perler, Cell 92:1-4 (1998).
Hall, et al., Cell 91:85-97 (1997).
Evans, et al., J. Biol. Chem., 274:18359-18363 (19991).
Mathys, et al., Gene, 231:1-13 (1999).
Otomo, et al., NMR 14:105-114 (1999).
Wood, et al., Nat. Biotechnol. 17:889-892 (1999).
Yamazaki, et al., J. Am. Chem. Soc. 120:5591-5592 (1998).
Mar. 7, 2003 Communication From the EPO in connection with corresponding EPO Application Serial No. 00 973 923.6 European Search Report received by Applicants Office Mar. 27, 2003.
Daugelat and Jacobs, Protein Science, 8:644-653 (1999).
Yonezawa, et al., Microbiol. Immunol. 39:243-247 (1995).

* cited by examiner

A TYPICAL PROTEIN SPLICING PRECURSOR AND PRODUCTS

Plate E. coli transformants
on LB agar + Drug (Ofloxacin)

Chromosomal GyrA: Drug$^r$
Plasmid GyrA: active
Host dies by poisoning

Splicing

Plate E. coli transformants
on LB agar + Drug (Ofloxacin)

Chromosomal GyrA: Drug$^r$
Plasmid GyrA: inactive
Host can grow

No Splicing lane 1: no plasmid
lane 2: E. coli GyrA
lane 3: intein inserted in E. coli GyrA
lane 4: dead intein in E. coli GyrA

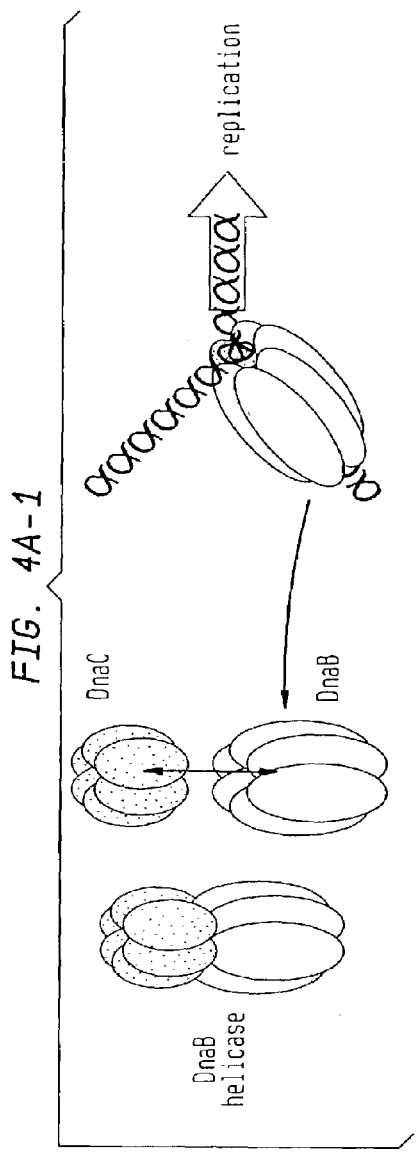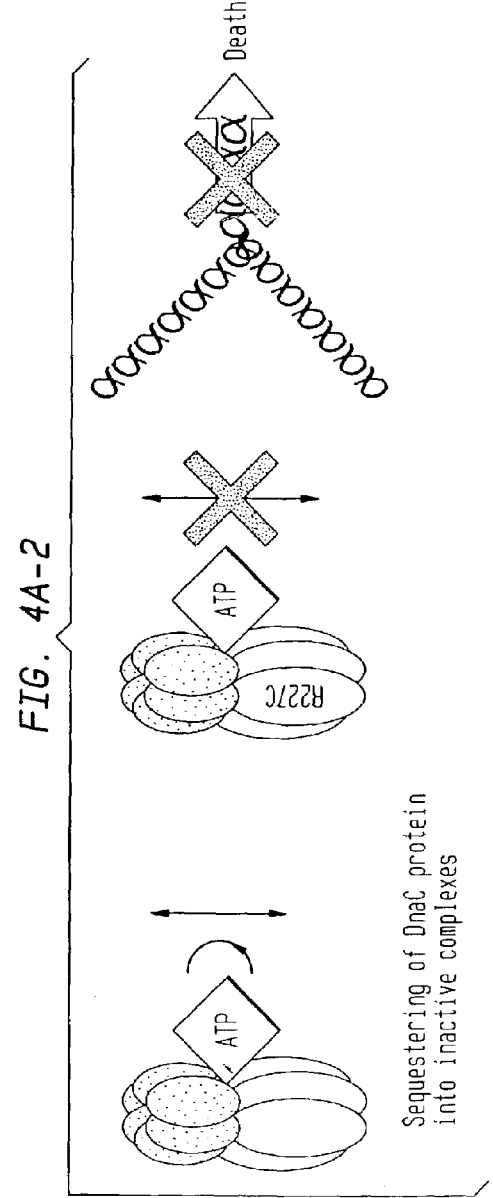

Splicing

No Splicing

FIG. 4D

```
E. coli DnaB vs. Mtu DnaB Exteins

PPHSTEAEQSVLGGLMLDNERWDDVAERVVADDFYTRPHRHIFTEMARLQESGSPIDLITILAESLERQGQLDSVGGFAYLAELSKNTPSAANISAYADIV
|:  |||||||:|  |||||:  ||||  | : |   |||||| :|||  |  | : ||||:||||    ||||||     ||:  |||||
PPQDLAAEQSVLGGMLLSKDAIADVLERLRPGDFYRPAHQNVYDAILDLYGRGEPADAVTVAAELDRRGLLRRIGGAPYLHLISTVPTAANAGYYASIV

RERAVVREMISVANEIAEAGF..DPQGRTSEDLLDLAESRVFKIAESRANKQEGPKNIADVLDATVARIEQLFQQPHDGVTGVNTGYDLNKKTAGLQPSD
|:|:    ||:  |  ||:|     | :|  :|      |  |: :|        ||| |:      ||   |:   |  :|:||  ::||
AEKALLRLVEAGTRVVQYGYAGAEGADVAEVVDRAQAEIYDVADRRLSEDF..VALEDLQPTMDEIDAI..ASSGGLARGVATGFTELDEVTNGLHPGQ

┌─────┐
                    │LIIVAARP│ SMGKTTFAMNLVENAAMLQDKPVLIFSLEMPSEQIMMRSLASLSRVDQTKIRTGQLDEDEWAHISGTMGTLLEKRNIYIDDSSGLPTEVRS
                    │|||||||│                      .||||||:  ||||| |  ||:||  ||| |  |:|:||||:     |    ||   :|: ||:   |  ||
                    │:IVAARP│ GVGKSTLGLDFMRSCCSIRHRMASVIFSLEMSKSEIVMRLLSAEAKIKLSDMRSGRMSDDDWTRLARRMSEISE.APLFIDDSPNLTMEIRA
                    └─────┘                                                                                 ┌────────────┐
                                                                                                          │DLRESGSIEQDAD│LIMFYRDEVYH
RARRIAREHGGIGLIMIDYLQLMRVPALSDNRTLEIAEISRSLKALAKELNVPVVALSQLNRSLEQRAQKRPVNS                              │||||||||||||│:||||:
||||:|||  ||:  ||  |||||    ||:|    ||||  :||  |||  ||   |  |::                                         │DLRESGSLEQDAD│WILLHRPDAFQ
KARRL.RQKANLKLIVVDYLQLMTSGKKYESRQVESFSRHLKLLAKELEVPVVATSQLNRGGPEQRTDKKPMLAD                              └────────────┘
                                                                                                                ↑
                                                                                                             intein ENSDLKGIAEIIIGKQRNGPIGTVRLTFNGQWSRFDNYA
|||:|   |:||||   |: |||  ||| |
RDDPRGGEADFILAKHRNGPTKTVTVAHQLHLSRFANMA Identity: 38%
```

Anti-T7 tag Western blot (T7 Tag at N-terminus of Mtu DnaB extein).
Black Boxes = extein, white box = intein. Top band = precursor,
middle band = C-terminal cleavage product, bottom band = spliced exteins

FIG. 7

The effect of the single amino acid preceding the Mxe GyrA intein in a heterologous extein context on splicing and N-terminal cleavage by DTT[a].

| -1 Amino Acid | % Spliced Products (19°C) | % Wild Type Rate DTT Cleavage | % DTT Cleavage Overnight |
|---|---|---|---|
| Tyr | 83 | 100 | 73 |
| Phe | 86 | 134 | 72 |
| Trp | 54 | 114 | 83 |
| Lys | 41 | 107 | 86 |
| Arg | 36 | 162 | 77 |
| Met | 30 | 132 | 81 |
| Leu | 16 | 126 | 95 |
| His | 7 | 88 | 86 |
| Gln | 15 | 29 | 97 |
| Cys | 13 | 22 | 97 |
| Ala | 10 | 20 | 93 |
| Ile | 3 | 5 | 64 |
| Pro | 1 | 4 | 39 |
| Val | 0 | 8 | 81 |
| Asn | 0 | 18 | 96 |
| Thr | 0 | 11 | 91 |
| Glu | 0 | 5 | 45 |
| Gly | 5 | 22 | 99 |
| Ser | 0 | 2 | 24 |
| Asp | 0 | ND | 100 |

[a] The Mxe GyrA intein was inserted between the maltose binding protein and a fragment of Dirofilaria immitis paramyosin (Telenti, et. al., (1997). J Bacteriol 179, 6378-82; Southworth, et. al., (1999). BioTechniques (in press)). This fusion protein was expressed in E. coli at 19°C to examine splicing or at 37°C (a non-permissive temperature for splicing of this precursor) to examine activation of the N-terminal splice junction for cleavage by DTT (dithiothreitol). Samples expressed at 37°C were incubated at 19°C in the presence of 50 mM DTT and (1) the rate of DTT cleavage at the N-terminal splice junction was quantitated as a percent of the DTT cleavage rate of each precursor compared to the precursor with the wild type -1 amino acid (Tyr) preceding the intein or (2) the amount of cleaved product after an overnight incubation in DTT. (ND = not determined).

FIG. 9

METHODS OF SELECTING FOR AGENTS THAT INHIBIT OR ACTIVATE PROTEIN SPLICING

A. Selection of agents that inhibit splicing of active inteins

| Scheme | Intein Minus Gene | Intein Plus Gene | Result of Selection |
|---|---|---|---|
| 1 | Resistant to drug | Dominantly sensitive | Agent that blocks splicing allows growth when drug present to drug |
| 2 | Wild type or non-toxic | Dominant lethal | Agent that blocks splicing allows growth |
| 3 | Conditionally essential product can be inactivated under defined conditions | Protein product is always expressed | Agent that blocks splicing results in cell death in the absence of the active intein minus product |

B. Selection of agents that activate splicing of inactive inteins

| Scheme | Intein Minus Gene | Intein Plus Gene | Result of Selection |
|---|---|---|---|
| 4 | Resistant to drug | Dominantly sensitive | Agent that activates splicing blocks growth when drug present to drug |
| 5 | Wild type or non-toxic | Dominant lethal | Agent that activates splicing blocks growth |
| 6 | Conditionally essential product can be inactivated under defined conditions | Protein product is always expressed | Agent that activates splicing results in cell growth in the absence of the active intein minus product |

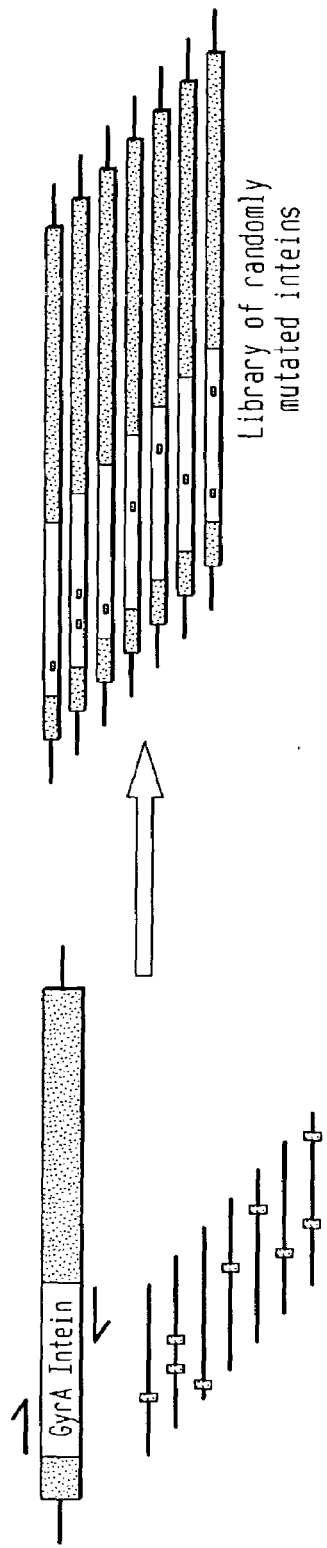

TEMPERATURE SENSITIVE Mxe GyrA INTEIN MUTANTS
ONLY SPLICE WHEN SHIFTED TO LOWER TEMPERATURE

Lanes A: Induction at nonpermissive temperature (37 °C), 3 hours.
Other lanes: Induction 37 °C, 3 hours, then shift to 16 °C overnight
Black Boxes: E. coli GyrA extein. White Box: Mxe GyrA intein
Coomassie blue stained gel.

FIG. 13

Mxe GyrA INTEIN TEMPERATURE SENSITIVE MUTATIONS

```
      Block A
 ┌─────────────┐
 │CITGDALVALPEG│ESVRIADIVPGARPNSDNAIDLKVLDRHGN
 └─────────────┘                  │
                                  S
                          Block B
                        ┌────────────┐
 PVLADRLFHSGEHPVYTVRTVE│GLRVTGTANHPLL│CLVDVAGV
   │                   └────────────┘   │  │
   A                                    A  M PTLLWK1IDeiKPGDYAVIQRSAFSVDCAGFArGkPeFAPTTY
       │││ ││                    │ │ │
       EP  GT                    H E G TVGVPGLVRFLEAHHRDPDAQAIADeLTDGRFYYAKVASVTDA
          │                │   │          │
          S                G   R          V
      Block B
     ┌──────────────────────────┐
 GVQ │PVYSLRVDTADHAFiTNGFVSHN T │
     └──────────────────────────┘
         │      │      │
         M      T      R
```

Temperature sensitive mutations are indicated below the wild type sequence.
Lower case letters indicate two amino acid mutations in one clone.

Mxe GyrA INTEIN TEMPERATURE SENSITIVE MUTATIONS

⊘ double amino acid change

○ single amino acid change

SCREENING AND USE OF AGENTS WHICH BLOCK OR ACTIVATE INTEIN SPLICING UTILIZING NATURAL OR HOMOLOGOUS EXTEINS

RELATED APPLICATIONS

This Application is a Divisional of application Ser. No. 09/430,221 filed Oct. 29, 1999, now U.S. Pat. No. 6,521,425 issued Feb. 18, 2003, which is a Continuation-In-Part of application Ser. No. 08/811,492, filed Mar. 5, 1997, now U.S. Pat. No. 5,834,247, issued Nov. 10, 1998, which is a Continuation-In-Part of application Ser. No. 08/580,555 filed Dec. 29, 1995, now abandoned, which is a Continuation-In-Part of application Ser. No. 08/496,247 filed Jun. 28, 1995, now abandoned, which is a Continuation-In-Part of application Ser. No. 08/146,885, filed Nov. 3, 1993, now abandoned, which is a Continuation-In-Part of application Ser. No. 08/004,139, filed Dec. 9, 1992, now U.S. Pat. No. 5,496,714, issued Mar. 5, 1996, the disclosures of each of which are hereby incorporated by reference herein.

BACKGROUND OF THE INVENTION

The present invention relates to the screening for and use of agents which either inhibit or activate protein splicing of inteins (IVPS). Specifically, disclosed herein is the development of 2 specific reporter systems for Gyrase A and DnaB inteins. Agents screened for in accordance with the present invention can be used to control protein splicing for any purpose, in vivo or in vitro, including antimicrobial activity of organisms containing inteins in essential genes. More specifically, the present invention relates to the use of inteins expressed in modified or unmodified native protein splicing precursors or homologous extein systems to screen for mutations that modulate splicing or agents that inhibit or activate splicing. The present invention improves on current reporter systems used to screen for agents that can control splicing by using a modified or unmodified native precursor or precursor homolog in order to take advantage of the more native intein active site formed by natural precursors or inteins in homologous exteins, since agents that are derived from non-native precursors may not have the identical selected activity on native precursors.

Production of mature proteins involves the flow of information from DNA to RNA to protein. Precise excision of DNA and RNA elements which interrupt that information has been previously described (M. Belfort, *Annu. Rev. Genet.* 24:363 (1990); T. R. Cech, *Annu. Rev. Biochem.* 59:543 (1990); Hunter et al., *Genes Dev.* 3:2101 (1989)). More recently, evidence for the precise excision of intervening protein sequences has also been described for the TFPI allele from *Saccharomyces cerevisiae* (Hirata et al., *J. Biol. Chem.* 265:6726 (1990); Kane et al., *Science* 250:651 (1990)) and the recA gene from *Mycobacterium tuberculosis* (Davis et al., *J. Bact.* 173:5653 (1991); Davis et al., *Cell* 71:1 (1992)). Each of these genes contains internal in-frame peptide segments which must be removed to produce the mature protein. Expression of Tfp1 and RecA each results in two peptides: one representing the intervening protein sequence (IVPS) and the other the ligated product of the external protein sequences (EPS). In 1994, the terms "intein" and "extein" were adopted in place of IVPS and EPS, respectively (Perler, et al., Nucleic Acids Res. 22:1125–1127 (1994)). This post-translational processing event has been termed "protein splicing". Similarly, the "Vent"® DNA polymerase gene from the hyperthermophilic archaeon *Thermococcus litoralis* contains two in-frame IVPS (Perler, et al., PNAS 89:5577 (1992)) and the DNA polymerase gene from the hyperthermophilic archaeon *Pyrococcus* species GB-D contains one intein (Xu, M., et al., Cell 75, 1371–1377 (1993)).

Over 80 inteins have been identified in bacteria, archaea and eucarya (Perler, F. B., et al. Nucleic Acids Res 25, 1087–93 (1997), Dalgaard, J. Z., et al., J Comput Biol 4, 193–214 (1997), Pietrokovski, S., Protein Sci. 7, 64–71 (1998) and Perler, F. B. Nucleic Acids Res. 27, 346–47 (1999). Four inteins have been found in *Mycobacterium leprae* (Davis, E. O., et al., EMBO J. 13, 699–703 (1994) and Smith, D. R., and et al. Genome Res 7, 802–19 (1997)) and three inteins in *Mycobacterium tuberculosis* (Cole, S. T., et al. Nature 393, 537–44 (1998)). One intein has been found in *Candida tropicalis* (Gu, et al., *J. Biol. Chem.*, 268(10): 7372–7381 (1993)).

Controllable IVPS (CIVPS) and methods for using the same to modify, produce and purify target proteins has been described (Comb et al., U.S. Pat. No. 5,496,714, issued Mar. 5, 1996; Comb et al., U.S. Pat. No. 5,834,247, issued Nov. 10, 1998). Methods for using inteins to screen for peptides (or derivative, analogic or mimetic thereof) or any agent that can enter cells to block or activate splicing of a natural or experimental reporter protein have also been described (U.S. Pat. No. 5,834,247, supra.. at Example 17). These methods specifically describe the screening of peptides using mycobacterial inteins as targets. The preparation of an in vivo peptide library utilizing chicken α-spectrin is also described.

While a general method of screening for antimicrobial agents using the *M. tuberculosis* RecA intein in a thymidylate synthetase (TS) reporter system has been described (Belfort, U.S. Pat. No. 5,795,731, issued Aug. 18, 1998), this system suffers from several limitations. Importantly, several studies of protein splicing in foreign contexts (such as the Belfort system) indicate that intein splicing is more efficient in the native extein than in foreign exteins (Xu, EMBO J. 13:5517–5522 (1994), Xu, EMBO J. 15:5146–5153 (1996), Telenti, J. Bacteriol. 179:6379–6382 (1997), Chong J. Biol. Chem, 273:10567–10577 (1998), Liu, FEBS Lett. 408: 311–314 (1997), Wu, Biochim. Biophys. Acta 1387:422–432 (1998B), Nogami Genetics, 147:73–85 (1997), Kawasaki J. Biol. Chem., 272:15668–15674 (1997), Derbyshire, Proc. Natl. Acad. Sci USA, 94:11466–11471 (1997), Southworth, BioTechniques 27:110–121 (1999), FIG. 7)). For example, the use of foreign exteins yields temperature-dependent splicing of the Psp-GBD Pol, Mxe GyrA and Synechocystis DnaB inteins (Xu, EMBO J. 13:5517–5522 (1994), Xu, EMBO J. 15:5146–5153 (1996), Telenti, J. Bacteriol. 179:6379–6382 (1997), Chong J. Biol. Chem, 273:10567–10577 (1998), Liu, FEBS Lett. 408: 311–314 (1997), Wu, Biochim. Biophys. Acta 1387:422–432 (1998B), Nogami Genetics, 147:73–85 (1997), Kawasaki J. Biol. Chem., 272:15668–15674 (1997) and Southworth, BioTechniques, 27:110–121 (1999), and FIG. 7).

While not wishing to be bound by theory, it is believed that such inefficient protein splicing in the foreign extein context occurs because the flanking extein is, in effect, the substrate of the intein. It is, therefore, likely that the intein may exhibit substrate specificity like all other enzymes. The substrate specificity of the intein limits acceptable extein sequences, hence the native extein sequence is the optimal substrate, whereas foreign extein sequences may not be acceptable substrates at all. For example, studies of the Sce VMA and Mxe GyrA inteins indicate that thiol induced N-terminal splice junction cleavage and splicing are, to varying extents, dependent on the single extein residue preceding the intein (Chong, J. Biochem. 273:10567–10577 (1998), Southworth, BioTechniques, 27:110–121 (1999)). Other extein residues have also been shown to affect splicing of the Sce VMA intein (Nogami Genetics, 147:73–85 (1997), Kawasaki J. Biol. Chem., 272:15668–15674 (1997)).

Additionally, exteins may affect the packing at the intein active site, or global folding of the intein and/or precursor, hence the use of a foreign extein may result in improper folding of the intein or precursor and inefficient or no splicing. Moreover, expression of an extein gene that naturally contains an intein in a foreign host, for example *E. coli* or yeast, may not be efficient (Perler et al. Proc. Natl. Acad. Sci. USA 89:5577–5581 (1992) and Hodges, et al., Nucleic Acid Res. 20:6153–6157 (1992)), whereas expression of the homologous endogenous extein is likely to be more efficient. For example, the *Mycobacterium leprae* RecA intein fails to splice in *E. coli*, while it splices in *M. leprae* (Davis, et al., EMBO J., 13:699–703 (1994)). It is possible that the *M. leprae* RecA intein would splice in *E. coli* RecA, although that has yet to be tested. In another example, the Synechocystis sp. strain PCC6803 DnaB gene, containing an intein, was unclonable in *E. coli* (Wu, et al., Proc. Natl. Acad. Sci. USA 95:9226–9231 (1998)). The *M. leprae* GyrA precursor did not splice efficiently in *E. coli* and was mostly insoluble, while the homologous Mxe GyrA intein spliced efficiently in *E. coli* GyrA.

Additionally, the use of homologous exteins would eliminate, in many instances, the need to introduce silent mutations in the reporter gene in order to insert the desired intein (see Belfort, supra., Comb, supra, Example 17). Homologous exteins may have naturally-occuring, conserved restriction enzyme sites that would allow the cloning of the intein into the homologous extein or they may have enough extein similarity to allow insertion of the intein into the homologous extein by recombination. Such systems also eliminate the need for an exogenous reporter gene, since innate extein properties of the native extein may be used for selection. Alternatively, the native extein may be mutated, either de novo or based on mutations in similar extein genes, to make the extein into a selectable marker or reporter gene.

Accordingly, the most desirable intein splicing systems would be those systems which express an intein from one organism in the homologous extein from the foreign host organism used for expression or to express the native precursor gene in a suitable foreign host organism.

Such intein systems would not only be useful in the screening of antimicrobial agents which inhibit intein splicing within a reporter gene (as described in Belfort, supra, Comb, supra..), but as controllable targets to direct expression of an extein product. Agents, for example peptides, that block intein splicing may be used to limit the expression of an extein in such systems. The suppression of such expression may be highly useful in the drug delivery context, where, for example, one wishes to turn on an enzyme which is active in killing cancer cells, or by delivering needed activity, for example insulin.

Similarly, such intein systems may utilize splicing-incompetent inteins to screen for agents with the ability to activate splicing.

SUMMARY OF THE INVENTION

In accordance with the present invention, there is provided selection systems and methods for selecting or screening for mutations or agents that control the splicing of inteins which comprise use of the intein's native host protein (extein) or a homologous extein in any host organism (FIG. 8). Specifically, in one preferred embodiment, there is provided a positive genetic selection system for the screening of agents which inhibit protein splicing which comprises: a host cell which contains (1) a copy of the extein gene (either episomal, chromosomal or synthetic) gene encoding a mutant or naturally drug-resistant form of a target enzyme (which as used herein includes not only enzymes, but proteins, peptides or the like), and (2) a wild-type or mutant form of the extein gene (either episomal, chromosomal, or synthetic) encoding a drug-sensitive form of the target enzyme which is dominantly cytotoxic upon interaction with the drug, wherein the gene encoding the drug-sensitive form of the target enzyme contains an intein, and wherein the inhibition of splicing of the drug-sensitive form of the target enzyme by a given reagent results in the survival of the host cell in the presence of the drug. In one specific embodiment, a positive genetic selection system which utilizes the *M. xenopi* GyrA intein is provided. This system is also applicable to any GyrA intein inserted at the same or different site in the GyrA extein gene.

In accordance with another preferred embodiment, there is provided a similar positive genetic selection system for the screening of agents which inhibit protein splicing which comprises a host cell which contains (1) a copy of the extein gene (either episomal, chromosomal or synthetic) encoding a wild type form of a target enzyme, and (2) a gene encoding a dominant cytotoxic form of the target enzyme (either episomal, chromosomal or synthetic) wherein the gene encoding the dominantly and cytotoxic form of the target enzyme contains an intein, and wherein the inhibition of splicing of the cytotoxic form of the target enzyme by a given reagent results in the survival of the host cell. In one particularly preferred embodiment, a positive genetic selection system which utilizes the *M. tuberculosis* DnaB helicase intein is provided. This positive selection system may also employ any DnaB intein inserted at the same or different site in the DnaB extein gene. Similar systems and methods of screening for agents that activate protein splicing are also provided, as are reporter systems utilizing native or homologous exteins and systems utilizing inteins.

Also provided by the present invention are methods of controlling in vivo expression of proteins by modulating protein splicing with inhibiting or activating agents. Similar methods of controlling the delivery of proteinaceous drugs in vivo by modulating protein splicing are also provided.

As used herein, "agent" includes, but is not limited to, a peptide (free or displayed on a scaffold such as chicken α-spectrin), a peptide derivative, analogic or mimetic, a natural product or a synthetic molecule.

BRIEF DESCRIPTION OF THE DRAWINGS

FIG. 4A-1 is a diagram depicting the intersection of DnaB with DnaC which is required to load DnaB onto the DNA replication machinery.

FIG. 4A-2 is a diagram depicting the sequestration of DnaC by a mutant E. coli DnaB helicase which leads to disrupted DNA replication and cell death.

FIG. 4D is an amino acid sequence comparison of part of the E. coli DnaB helicase (SEQ ID NO:3) and M. tuberculosis DnaB helicase (SEQ ID NO:4) sequences indicating that the amino acid sequences are very similar and that the site in E. coli DnaB that was mutated to make it cytotoxic is conserved in M. tuberculosis DnaB (first on larged sequence) and that the intein insertion site is also conserved in E. coli DnaB (marked by the arrow).

FIG. 7 is a table showing the effect of the single amino acid preceding the Mxe GyrA intein in a heterologous extein context on splicing and N-terminal cleavage by DTT.

FIG. 9 is a summary of the various methods of selecting agents that inhibit or activate protein splicing. Each system is based on a merodiploid cell containing an intein plus and an intein minus extein gene.

FIG. 10 depicts the scheme for creating random mutations in the Mxe gyrA intein by error prone PCR of the intein followed by cloning of the mutated intein genes into the E.coli Mxe gyrA extein.

FIG. 13 illustrates the Mxe GyrA intein sequence (SEQ ID NO:46) with mutations found in the temperature sensitive splicing clones indicated below the wild-type residue.

DETAILED DESCRIPTION

The present invention is directed to methods of selecting or screening for mutations or agents that block or activate protein splicing of inteins using natural precursors or by inserting inteins in homologous extein genes. These mutations or agents can be used to activate or keep inactive enzymes in vivo or in vitro for pharmacological, chemotherapeutic, or biotechnological purposes. In contrast, these same methods can be used to select agents that block or activate splicing in a non-homologous extein if no genetic selection system or screen can be generated for the native extein protein.

The in vivo control of protein splicing mediated by a blocking or activating peptide, or other agent that can enter a cell, acting on a controllable intervening protein sequence (CIVPS) has been described (U.S. Pat. No. 5,834,247, supra. at Example 17). In the present invention, it should be noted that a non-controllable IVPS, or intein, is used to identify agents that will convert the IVPS into a CIVPS. The blocking of such splicing activity by specific agents such as peptides or natural products, and analogues thereof, is particularly useful in combating pathogens such as *Mycobacterium tuberculosis, Mycobacterium leprae, Mycobacterium avium*, or *Candida tropicalis* by blocking the splicing of essential proteins in those organisms.

Approximately 97 inteins have been identified and are available from public databases (Perler, Nucleic Acids Res. 22:1125–1127 (1994), Perler, Nucleic Acids Res. 27:346–347 (1999), Pietrokovski, S., Protein Sci., 7:64–71 (1998) and Dalgaard, et al., J. Comput. Biol., 4:193–214 (1997). Sequencing projects of small prokaryotic genomes (e.g., *Mycobacterium tuberculosis, Mycobacterium leprae*, and *Methanococcus jannaschii*) already account for the majority of published intein sequences. Host genes of these inteins are often involved in such essential cellular functions as DNA replication, expression, or various metabolic processes (compiled in: Perler, Nucleic Acids Res. 25:1087–1093 (1997), Perler, Nucleic Acids Res. 27:346–347 (1999), Pietrokovski, S., Protein Sci., 7:64–71 (1998) and Dalgaard, et al., J. Comput. Biol., 4:193–214 (1997). Hence, the disruption of these essential functions via the blocking of intein splicing by peptides, or other agents, represents a means by which to screen for anti-microbial and anti-pathogenic agents.

Figure 2:
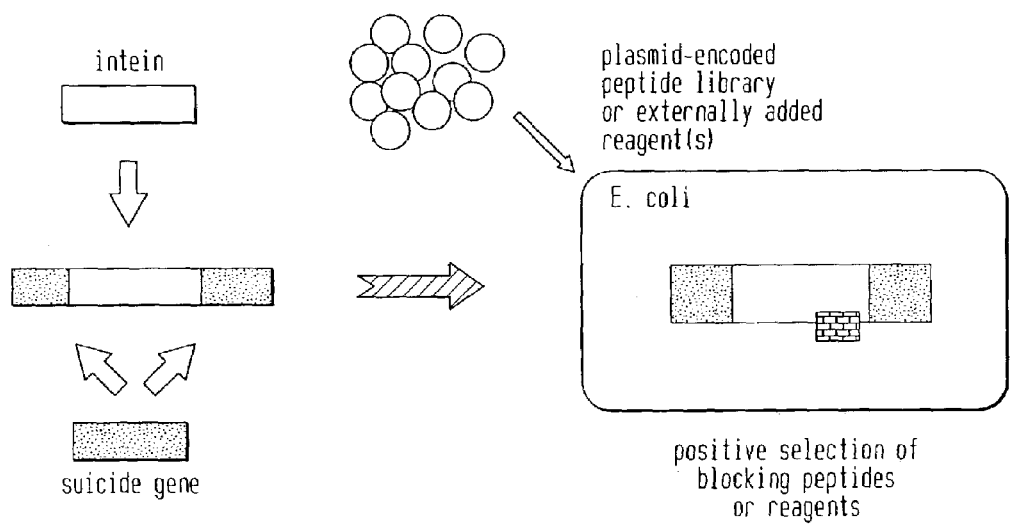
FIG. 2 is a diagram depicting a general scheme for the selection of peptides which block intein splicing of a dominant lethal suicide gene in vivo.

Generally, a positive selection system consists of a gene that is detrimental to a host organism depending on the growth media or the host strain genetic background. The gene product is toxic for the cell, inhibiting growth or killing the host unless the gene product is inactivated. In the context of a protein splicing genetic system, a positive selection system is defined as a system that allows selection against the splicing of an intein inserted in-frame into a host gene (see FIG. 2). If splicing occurs in the precursor protein containing the intein, the cytotoxic host protein will be active and inhibit cell growth or kill the cell; if splicing is disrupted the cytotoxic host protein will be inactive and allow cell growth. The same description applies to reporter systems where detection of the host protein is scored, rather than selection for organism viability. Many reporter genes are known, the most common example is the Blue/white screen involving β-galactosidase function on X-gal to produce a blue color.

In accordance with one embodiment of the present invention, there is provided a positive selection system for identifying agents which block or activate protein splicing which comprises a host cell which contains (1) a copy of the extein gene (either episomal, chromosomal or synthetic) encoding a mutant or naturally drug-resistant form of a target enzyme; and (2) a wild type or mutant form of the extein gene (either episomal, chromosomal or synthetic) encoding the target enzyme that is sensitive to the drug, into which is inserted an intein, wherein the spliced form of the intein-containing target enzyme is toxic to the host organism upon interaction with a certain drug. In this system, the host cell so transformed will express the drug sensitive enzyme if the intein is properly spliced, resulting in reduced viability of the organism because the spliced product is dominantly lethal or cytotoxic to the host organism, despite the fact that the drug-resistant homologous gene is also expressed. The intein-les copy of the gene is required to maintain viability in cells in which splicing of the plasmid borne extein gene is blocked.

In one preferred embodiment, a plasmid-encoded, drug sensitive gene is the naturally occurring intein/extein precursor or its homolog containing an intein, which intein may be either naturally occurring or inserted, and drug sensitivity may be naturally occurring in this precursor gene or introduced by mutation in the extein portion of the gene. This system results in death of all cells where splicing occurs and thus provides a system for selecting for mutations, drugs, chemicals, peptides, etc. which block splicing in vivo since cell viability requires blockage of splicing.

Figure 3A:
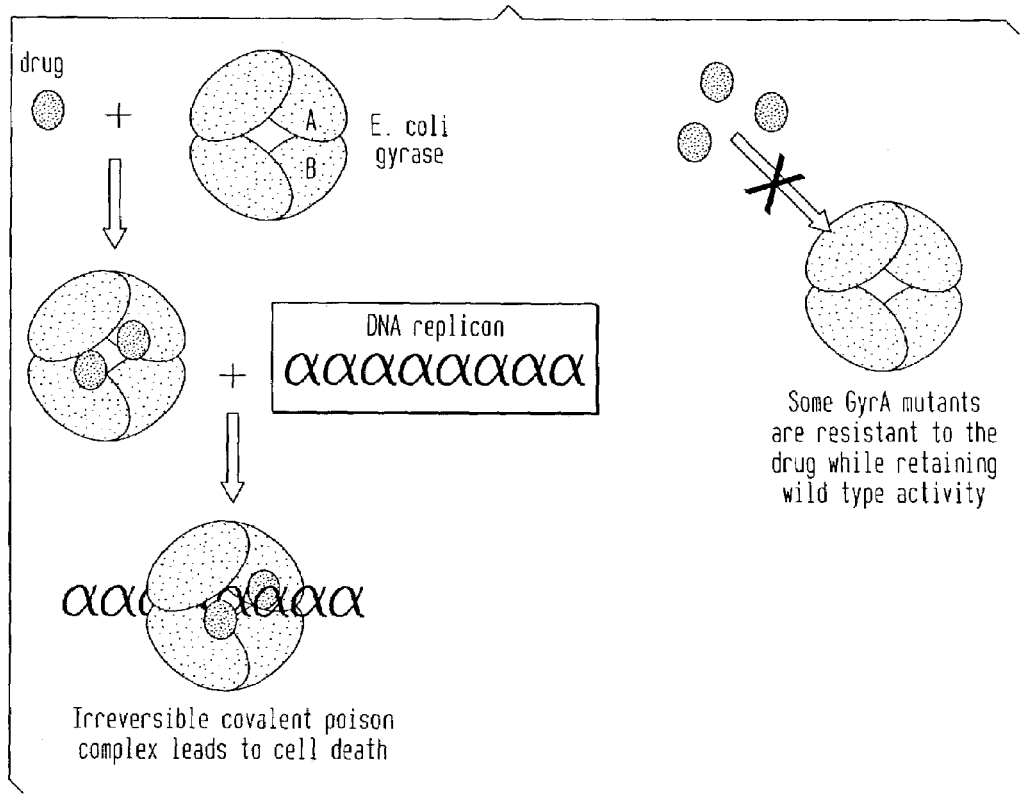
FIG. 3A is a diagram depicting the irreversible blocking of DNA replication by *E. coli* GyrA interaction with a drug (ofloxacin).

In a particularly preferred embodiment, the *Mycobacterium xenopi* GyrA intein (Mxe GyrA) (SEQ ID NO:11) (Telenti et al., J. Bacteriol. 179:6378–6382 (1997) is inserted into the homologous extein of *E. coli* GyrA (see FIG. 3D). In *E. coli*, GyrA is an essential gene that encodes for the A subunit of the *E. coli* gyrase hetero-tetramer protein complex. *E. coli* gyrase is a type II topoisomerase involved in DNA relaxation at the origin of replication of the bacterial chromosomal DNA (Swanberg and Wang, *J. Mol. Biol.* 197:729–736 (1987)). The wild type *E. coli* GyrA binds irreversibly to quinoline drugs such as ofloaxcin, preventing DNA relaxation during replication, and leading to cell death (see FIG. 3A). However, certain mutants of wild type *E. coli* GyrA are drug-resistant, while retaining gyrase activity. The generation of an *E. coli* GyrA merodiploid host cell which contains a chromosomal copy of a drug-resistant gyrA gene with a second intein-containing, drug sensitive gyrA gene results in a drug sensitive *E.coli* host, since in this case, drug sensitivity is dominant. The drug sensitive phenotype is dominant because the drug sensitive GyrA forms an irreversible covalent poison complex with the drug that interferes with DNA replication (FIG. 3A).

By merodiploid we mean that the cell contains an extra copy of a gene (or several genes) which has been introduced into the cell by any means known to one skilled in the art, such as transformation, infection, conjugation, plasmids, virus, phage, or by generating a transgenic strain and which may be present on either an episomal element or on the host chromosome.

In accordance with the present invention, there is further provided a similar type of positive selection system (for identifying agents which block or activate protein splicing) which comprises a host cell which contains (1) a copy of the extein gene (either episomal, chromosomal or synthetic) encoding a wild type form of a target enzyme, which expresses a non-toxic form of the extein protein; and (2) a second a extein gene (either episomal, chromosomal or synthetic) encoding a cytotoxic form of the target enzyme, into which is inserted an intein. In this system, the merodiploid host cell expresses the cytotoxic enzyme if the intein is properly spliced. Thus, cells must be treated with chemicals, agents or peptides that block splicing of the cytotoxic enzyme at all times when the cytotoxic enzyme is expressed. The cytotoxic extein must be dominantly lethal, as the intein-less copy of the extein gene is also expressed. The intein-less copy of the gene is required to maintain viability in cells in which splicing of the plasmid borne extein gene is blocked.

In one preferred embodiment, instead of using an intein inserted into a cytotoxic foreign extein homolog, the natural intein precursor may be mutated to produce a cytotoxic extein enzyme after splicing of the intein.

Figure 1:
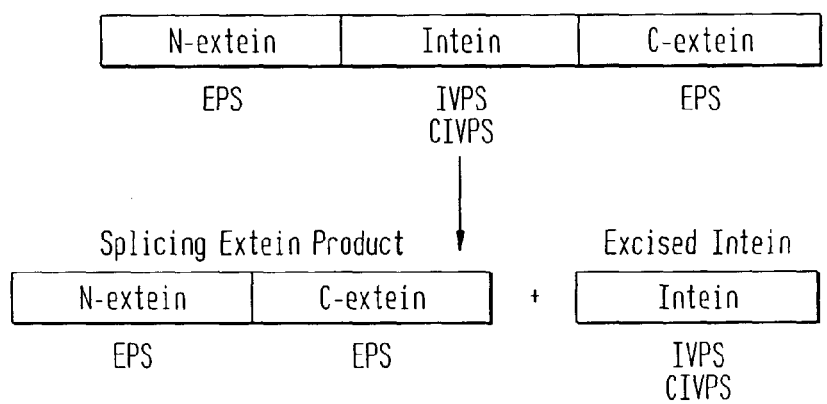
FIG. 1 is a diagram depicting a protein splicing precursor and products and alternative names for each element or part thereof.
Figure 4B:
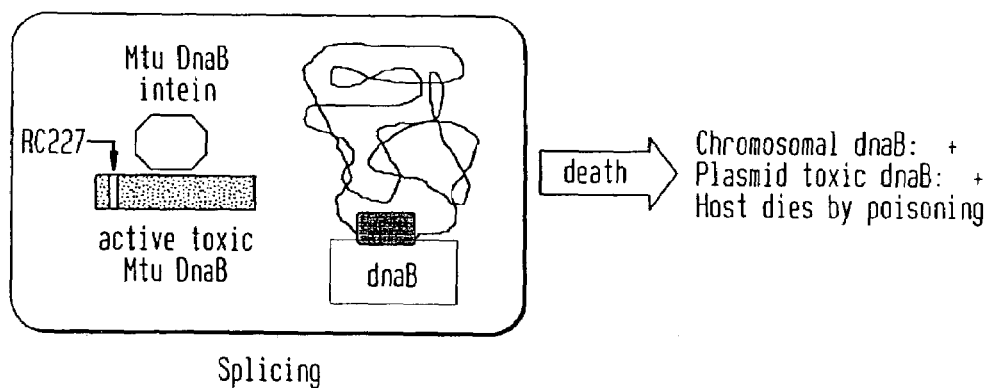
FIG. 4B is a diagram depicting a Mtu DnaB helicase intein-splicing system for the selection of agents which block intein splicing: the splicing of the Mtu DnaB helicase intein out of a dominant lethal mutant Mtu DnaB helicase extein produces mutant Mtu DnaB helicase which sequesters Eco DnaC and poisons replication despite the presence of the chromosomal Eco DnaB helicase, as a result, the host dies.

In a particularly preferred embodiment, the *Mycobacterium tuberculosis* DnaB precursor (Cole et al., Nature, 393:537–544 (1998)) is mutated in the extein region to a cytotoxic form based on the known cytotoxic mutation in *E.coli* DnaB, where Arg231 was mutated to Cysteine (Marszalek and Kaguni, J. Biol. Chem., 267:19334–19340 (1992) and Shrimankar, et al., J. Bacteriol., 174:7689–7696 (1992)). DNA helicases are essential proteins that unwind a DNA duplex to yield a single-stranded DNA intermediate required for replication, recombination, and repair (LeBowitz and McMacken, J. Biol. Chem., 261:4738–4748 (1986) and Lohman, Mol., Microbiol., 6:5–14 (1992)). The hexameric *E. coli* helicase encoded by the dnaB gene interacts with an hexameric DnaC complex and ATP. Some DnaB mutants are dominant lethal (Bouvier and Oreglia, C. R. Acad. Sci. Hebd Seances Acad. Sci. D., 280:649–652 (1975) and Maurer and Wong, J. Bacteriol., 170:3682–3688 (1988), Saluja and Godson, J. Bacteriol., 177:1104–1111 (1995) and Sclafani, et al., Mol. Gen. Genet. 182:112–118 (1981)). The R231C mutant protein is deficient in ATP hydrolysis, helicase activity, and replication activity at the chromosomal origin of replication resulting in cell death. As shown in FIG. 4D, Mtu DnaB contains this same Arginine (R227), and mutating it to Cysteine renders the Mtu DnaB gene cytotoxic. This mutation is dominantly cytotoxic in *E. coli*, and both the *E.coli* and *M. tuberculosis* DnaB proteins result in sequestering of the *E. coli* DnaC protein into inactive complexes, preventing DnaC from 'loading' DnaB onto the *E. coli* DNA replication fork (see FIG. 4A-1 and FIG. 4A-2).

Both of the positive selection systems described in the present invention utilize either native or homologous foreign exteins in order to optimize protein splicing and avoid the ineffecient splicing which can result from insertion of the intein into non-homologous foreign extein.

Figure 6:
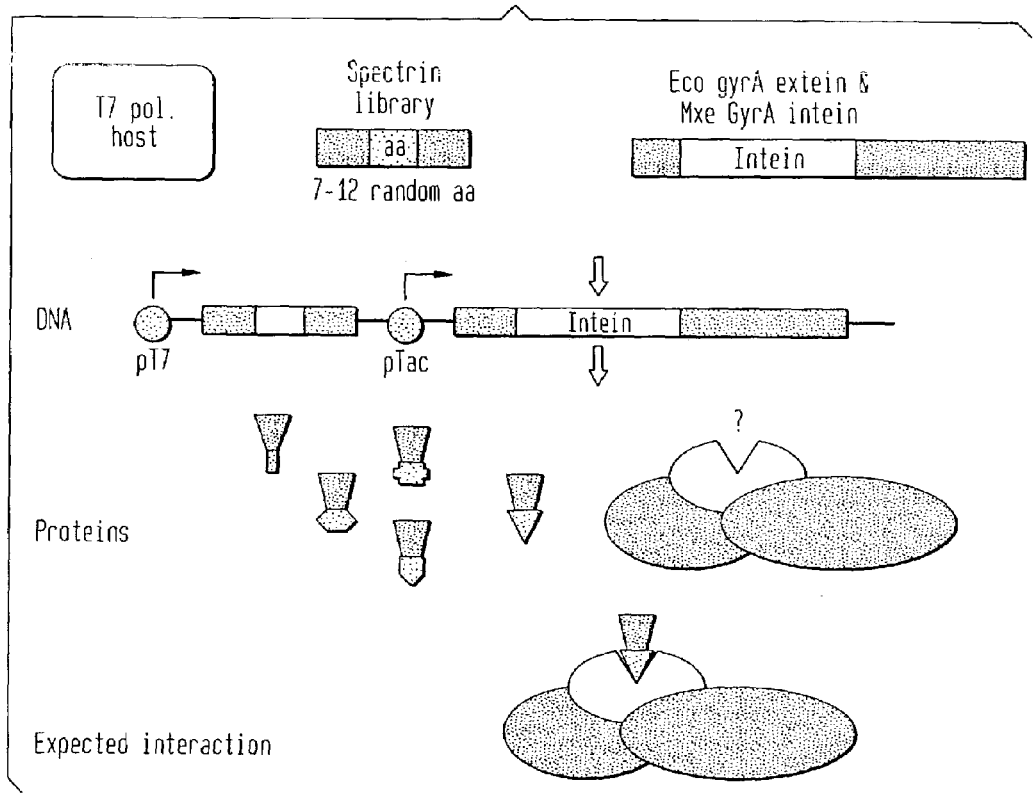
FIG. 6 is a diagram depicting the production of a combinatorial peptide library using chicken α-spectrin and the screening of these peptides for those that block Mtu DnaB intein splicing in Mtu DnaB. E. coli GyrA gyrase. "aa" represents a portion of spectrin which can be randomized. The spectrin scaffold is represented by a trapazoid and the different amino acid sequences by various other shapes. If the spectrin binds to the precursor, splicing is blocked. The system has three components: a host cell expressing T7 RNA polymerase, the spectrin library and the intein plus GyrA gene. The latter two genes are present on a single plasmid under control of T7 RNA polymerase promoters.

Co-transformation of the host cell in these positive selection systems with a plasmid engineered for the expression of an in vivo peptide library or transformation with a plasmid that contains both the selection marker and the in vivo peptide library (as in FIG. 6) allows for the direct selection of clones expressing a peptide that blocks (or alternatively activates) protein splicing. In vivo expression of peptides may be hampered by the host's efficient proteolytic degradation systems. Therefore, expression of these peptides in vivo in the context of larger proteins is preferred, especially in surface loop regions of larger proteins. In vivo expression of peptides fused to larger proteins has been achieved for example, in the catalytic loop of thioredoxin (Colas et al., Nature, 380:548–550 (1996)), and it is possible to express peptides fused within many different proteins. Peptides expressed in-frame in highly soluble, well expressed, thermostable, solvent-exposed loops of a protein are less subject to in vivo proteolysis or degradation and such fusions enhance the functional expression of peptides in a cell.

In a preferred embodiment, a combinatorial peptide library in a fragment of chicken α-spectrin is constructed, as previously described (see U.S. Pat. No. 5,834,247, supra at Example 17). The EF hand region of chicken α-spectrin was chosen because its structure is known, its EF hand domain forms a small protein with a stable structure, and it has a flexible surface loop. The structure of the chicken α-spectrin EF hand domain was elucidated by NMR analysis (Trave, et al., EMBO J. 14:4922–4931 (1995)). The term EF hand describes a type of protein tertiary structural motif consisting of a helix, a turn (loop) and a second helix. The EF hand domain of chicken α-spectrin is located at the carboxy terminus of chicken α-spectrin. Its 84 amino acid structure is arranged in two EF hand helix-turn-helix motifs separated by a 14 amino acid long flexible linker (SEQ ID NO:12). The protein is extremely soluble without any detectable precipitation or aggregation even at concentrations of up to 10 mM. The linker loop is mainly unstructured in solution and mutagenesis data show that minor deletions or insertions in the loop do not disturb the stabilizing hydrophobic interactions between the 2 EF-hand.

We have taken advantage of this last property to insert random peptides in the linker region between the chicken α-spectrin EF hands. Peptide libraries of various sizes can be investigated. It will be readily apparent to the skilled artisan that alternative methods of producing in vivo peptide libraries for screening may be utilized and are within the scope of the present invention.

Although the systems discussed above select for agents that block splicing of native or homologous exteins, it will be recognized by those of skill in the art that similar strategies can be used for screening with reporter genes to look for agents that inhibit expression of active reporter genes. It will likewise be recognized by the skilled artisan that similar strategies can be used to look for agents that activate splicing of a splicing-deficient intein in its native context or in a homologous extein gene, as long as the extein gene can be converted into a reporter. For example, in one embodiment, a reagent that activates a splicing-deficient precursor results in expression of an active reporter protein, resulting in inhibition of cell growth or detection of the active reporter protein.

Although the *Escherichia coli* (*E.coli*) GyrA and the *Mycobacterium tuberculosis* (*M. tuberculosis*) DnaB selection systems are described above, it will be recognized by the skilled artisan that any genetic selection system can also be used to isolate peptide sequences or other agents which disrupt or catalyze protein splicing. Likewise, although we describe the specific use of the *M. xenopi* GyrA intein (SEQ ID NO:11) and the *M. tuberculosis* DnaB intein (SEQ ID NO:13), the skilled artisan will recognize that this strategy is equally applicable to any intein (see, e.g., Perler, et al., Nucleic Acids Res. 27:346–347 1999)) present in its native or homologous context. It will likewise be readily apparent to those of skill in the art that alternative means of generating peptide libraries for screening may be used. It will likewise be recognized by the skilled artisan that in the absence of a selection or screening system for the native extein protein that similar strategies can be applied to splicing of inteins in less optimal heterologous extein systems.

Activating and/or inhibiting agents identified by the screening methods of the instant invention may also be used to control the in vivo expression of a target protein. Once the only copy of an active extein gene contains an intein, gene function can be inhibited if the organism is treated with an agent that blocks splicing. On the other hand, if a splicing-impaired intein is used, gene function can be activated if the organism is treated with an agent that activates splicing. The agents and splicing can be modulated at any time during the development and life of the organism by addition or removal of the splicing activating or inhibiting agent.

Similarly, controllable splicing may be used to deliver active proteins at specific times or to specific places. In many instances, therapeutic drugs can be cytotoxic to the host and would be best if only active at the target site. For example, chemotherapy drugs are often generally cytotoxic and adverse reactions in normal cells could be eliminated if the drug could be specifically activated in the tumor. If one has a drug that is at least partially proteinacious, an intein that can be activated or inhibited by a second agent, as described above, could be inserted into the protein portion of the therapeutic agent. The drug is then administered in an inactive form, and subsequently activated in the desired target tissue.

As noted above, it is believed that inefficient protein splicing in the foreign extein context occurs as inteins may exhibit substrate specificity, preferring their native extein sequence to that of foreign exteins. In accordance with another embodiment, there is provided a method of overcoming this limitation by employing an intein with one or more, preferably one to five, amino acid residues from its native extein. Inclusion of such amino acid residues may be at either or both ends of the homologous intein. Inclusion of amino acid residues from the native extein will facilitate methodologies of the present invention. Such amino acid residues from the native extein may be incorporated into the precursor by methods well known to those skilled in the art.

Insertion of a target intein in the heterologous extein may be at any of a number of sites, including but not limited to, a surface location in the extein, within a loop region of the extein, at a protease sensitive site, or a position known to facilitate insertion of additional amino acid residues without inactivating the extein.

The Examples presented below are only intended as specific preferred embodiments of the present invention and are not intended to limit the scope of the invention except as provided in the claims herein. The present invention encompasses modifications and variations of the methods taught herein which would be obvious to one of ordinary skill in the art.

The references cited above and below are hereby incorporated by reference herein.

EXAMPLE I

A Mxe GyrA Intein-Mediated Positive Selection System for Inhibition of Protein Splicing A Positive Selection System Based on Blocking Splicing of the Mxe GyrA Intein (IVPS) in *E. coli* GyrA: Background Gyrases are essential multimeric enzymes involved in DNA replication in bacteria (Swanberg and Wang, 1987). Both gyrase subunit A and B have been extensively studied as drug targets in bacterial human pathogens (e.g., *Mycobacteria, Salmonella, Enterbacteriaceae, Citrobacter, Pseudomonas, Streptococcus, Staphylococcus, Yersinia, Rhodobacter, Haemophilus, Neisseria, Providencia*). The GyrA subunit of gyrases can complex with quinoline drugs, such as ofloxacin, and induce cell death. The complex formation of quinolines with gyrase is followed by a rapid and irreversible inhibition of DNA synthesis, inhibition of growth, and induction of the SOS response (see FIG. 3A). At higher drug concentrations, cell death occurs as double-strand DNA breaks in the bacterial chromosome are released from trapped gyrase complexes.

In many gram-negative bacteria (e.g., *E. coli*), resistance to quinoline arises from mutation of the Gyrase A protein in the quinoline resistance determining region such as gyrA96 or gyrA83. Those mutations may involve Ser83 in *E. coli* GyrA. In a merodiploid cell containing a drug resistant gyrA gene (such as gyrA83) on the chromosome and a wild type (gyrA+) copy of gyrA on a plasmid, the wild type gene (drug sensitive) product of gyrA is dominant. By merodiploid, we mean that the cell contains an extra copy of a gene (or several genes) which has been introduced into the cell by any means known to one skilled in the art, such as transformation, infection, conjugation, plasmids, virus, phage, or by generating a transgenic strain and which may be present on either an episomal element or on the host chromosome. The wild type gyrA gene can be introduced into the cell by any means known to one skilled in the art and should not be considered limited to a plasmid. Many *E. coli* strains are available that contain gyrA mutants which are resistant to quinoline drugs such as ofloxacin. However, this system is also applicable to any other host system where (1) the chromosomal copy of the gyrA gene is resistant to quinoline drugs, (2) the introduced sensitive gyrA gene is present as the heterologous *E. coli* gyrA::Mxe gyrA intein fusion or the native Mxe gyrA or *M. leprae* gyrA genes, and (3) the intein containing drug sensitive gyrA gene is operably linked with the appropriate signals for expression in that host. Likewise, the Mxe GyrA intein could be inserted into the gyrA gene of any experimental host cell just as it was inserted into the *E. coli* gyrA gene. Likewise, any gyrA intein can be used in the above selection system, whether present at the same site as the Mxe GyrA intein or a different site.

Figure 3B:
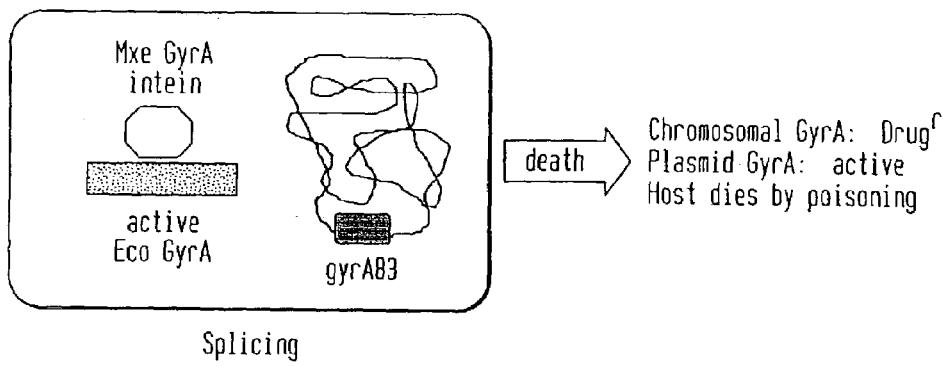
FIG. 3B is a diagram depicting a Mxe GyrA intein-splicing system for the selection of agents which block intein splicing. The splicing of the Mxe GyrA intein out of the homologous Eco GyrA extein produces a drug sensitive, wild-type Eco GyrA which, in the presence of ofloxacin, forms an irreversible covalent poison complex during replication that kills the cell, despite the presence of the chromosomal mutant GyrA which is drug resistant.

Since sensitivity to quinoline drugs is dominantly cytotoxic, in the presence of these drugs, a gyrA+/gyrA83 host cell is not viable because wild type GyrA proteins can still bind drug molecules and poison DNA replication (see FIG. 3B). The co-expression of a chicken α-spectrin peptide library (as described in U.S. Pat. No. 5,834,247 supra. at Example 17) allows for the positive selection of peptides that can disrupt splicing of the Mxe GyrA intein. Likewise, this system can be used to screen for any agent that inhibits splicing of the Mxe GyrA intein in vivo or for Mxe GyrA intein mutations that block splicing.

Figure 3C:
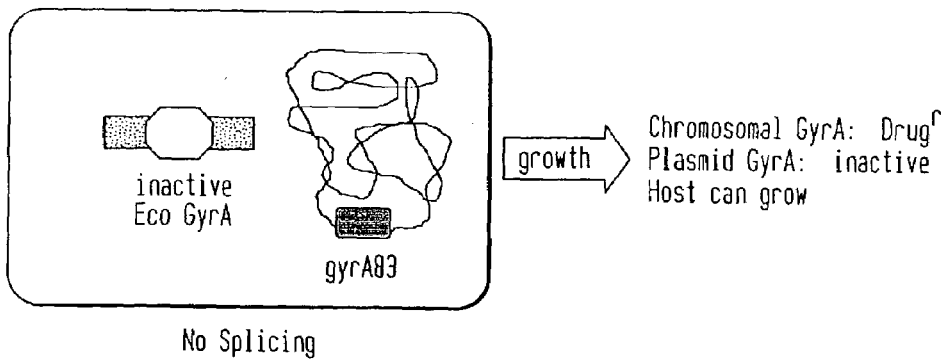
FIG. 3C is a diagram depicting a Mxe GyrA intein-splicing system for the selection of agents which block intein splicing: the blocking of splicing of the Mxe GyrA intein out of the homologous Eco GyrA extein results in the expression of the inactive drug sensitive Eco GyrA and the chromosomal mutant GyrA, which is ofloxacin-resistant. Hence, in the absence of an active drug sensitive Eco GyrA (due to the blockage of splicing,) the host grows.
Figure 3D:
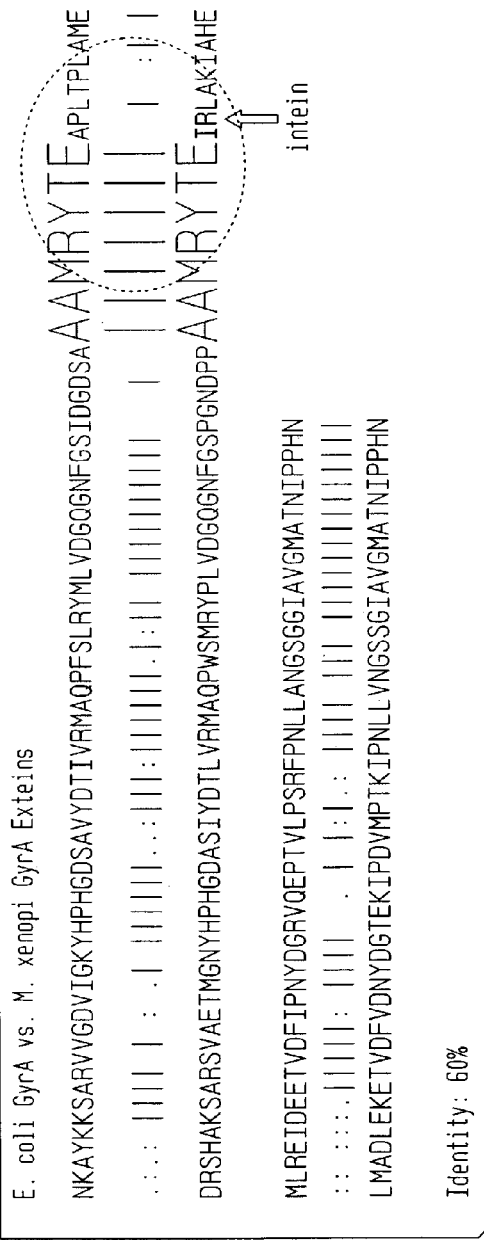
FIG. 3D is an amino acid sequence comparison of part of the E. coli GyrA (SEQ ID NO:1) and M. xenopi GyrA (SEQ ID NO:2) sequences, indicating that the GyrA exteins are very similar in amino acid sequence, especially at the intein insertion site marked by the arrow.

Insertion of the Mxe GyrA Intein (IVPS) Gene into the Homologous Site in the *E. coli* GyrA Gene In some Mycobacteria, the gyrase A subunit active site is often interrupted by a naturally occurring allelic intein (IVPS) near the active site tyrosine residue (e.g., *Mycobacterium flavescens, Mycobacterium gordonae, Mycobacterium kansasii, Mycobacterium leprae, Mycobacterium malmoense* and *Mycobacterium xenopi*, (Sander, et al., Microbiology, 144:589–591 (1998), Telenti, et al., J. Bacteriol., 179:6378–6382 (1997), Perler, et al., Nucleic Acids Res. 27:346–347 (1999), Southworth, BioTechniques, 27:110–121 (1999)). The *M. xenopi* (Mxe) GyrA intein (IVPS) utilized in the system described herein, lacks the endonuclease signature motifs and other sequences similar to homing endonucleases and has been extensively studied as a prototype minimal intein (IVPS) (Klabunde, et al., Nature Struct. Biol. 5:31–36 (1998), and Telenti, et al., J. Bacteriol., 179:6378–6382 (1997) and Southworth BioTechniques, 27:110–121 (1999)). The most favorable insertion site for the Mxe GyrA intein in *E. coli* GyrA is the homologous insertion site compared to the native Mxe GyrA extein, since it shares sequence identity with the native Mxe GyrA extein (FIG. 3D). The intein (IVPS) insertion site was chosen immediately upstream of the conserved tyrosine active site residue at position 122 in *E. coli* GyrA:

D S A <u>A A M R Y122</u> c i t    s h n <u>T123 E</u> I R <u>L</u> A K I
(SEQ ID NO:14)                  (SEQ ID NO:45)

Amino acid numbers refer to the position of the amino acids in *E. coli* GyrA (see SEQ ID NO:1 for a partial *E. coli*

GyrA sequence). The underlined amino acids (single letter amino acid code) are the amino acids identical in both E. coli and Mxe GyrA exteins (see FIG. 3D). The lower case letters represent Mxe GyrA intein (IVPS) amino acids. The dashes represent the remainder of the residues of the Mxe GyrA intein (IVPS) that are not listed (see SEQ ID NO:2, for the complete Mxe GyrA intein sequence).

First, the E. coli gyrA gene was cloned by polymerase chain reaction (PCR) using E. coli K12 genomic DNA under the following experimental conditions. A forward primer 5'-GATA GGCTAGCGATGAGCGACCTTGCGAGAG-3' (SEQ ID NO:15) and reverse primer 5'-TGAAGCAAT-TGAATTATTCTTCTTCTGGCTCG-3' (SEQ ID NO:16) were used in a PCR mixture containing 20 U/ml Vent® Exo+ DNA polymerase (New England Biolabs, Inc., Beverly, Mass.), 400 µM of each dNTP, 4 nM each primer and 100 ng of E. coli K12 genomic DNA. Amplification was carried out in a Perkin-Elmer/Cetus (Emeryville, Calif.) thermal cycler 480 for 1 min at 95° C. and then cycled at 45° C., 30 sec; 72° C., 2 min and 30 sec; 95° C., 30 sec for 20 cycles. The PCR products from one 50 µl PCR reaction and 2 µg of pCYB1 (IMPACT™ I kit, New England Biolabs, Inc., Beverly, Mass.) were separately digested with 250 U/ml of NheI and 1000 U/ml of MfeI in the presence of 100 µg/ml of BSA. The digestion was performed at 37° C. for 1 hour. Digested PCR products and plasmid DNA were separated by agarose gel electrophoresis and the excised bands further purified using QIAEX II beads as described by the manufacturer (Qiagen, Studio City, Calif.). Ligation was carried out at 20° C. for 1 hour using a 1:4 ratio of vector to insert and 40,000 U/ml of T4 ligase. Ligation products were transformed into E. coli strain ER2267 competent cells. Recombinant plasmids were checked by NheI/MfeI digestion which results in the excision of the cloned insert in properly ligated recombinants. One of the resultant correct plasmids containing the E. coli gyrA gene placed under transcriptional control of the pCYB1 pTac promoter was named pEA500. The gyrA insert was checked by DNA sequencing to insure that no sequence errors were introduced by PCR.

Second, to facilitate cloning of the Mxe GyrA intein into E. coli GyrA, unique silent NotI and XbaI restriction enzyme sites were engineered 7 bp and 44 bp, respectively, away from each side of the E. coli GyrA active site residue, Y122 of pEA500 by site-directed silent mutagenesis. The QuickChange kit was used following the manufacturer's instructions (Stratagene, La Jolla, Calif.) with mutagenic primers: NotI oligonucleotides: 5'-CGGCGACTCTGCG-GCCGCAATGCGTTATA CGG-3' (SEQ ID NO:17) and 5'-CCGTATAACGCATTGCGGCCGCA GAGTCGCCG-3' (SEQ ID NO:18), and XbaI oligonucleotides: 5'-GAACT-GATGGCCGCTCTAGAAAAAGA GACGG-3' (SEQ ID NO: 19) and 5'-CCGTCTCTTTTTCTAGAGCGGCCA TCAGTTC-3' (SEQ ID NO:20). The resultant plasmid containing E. coli GyrA with NotI and Xbal restriction enzyme sites was called pEA502.

Third, a 68 bp DNA cassette with flanking NotI/XbaI restriction sites was designed to be cloned into the pEA502 unique NotI/XbaI sites. This cassette introduced a unique BlpI silent restriction enzyme site 10 bp away from Y122 which subsequently allowed cloning of any intein (IVPS or CIVPS) near the E. coli GyrA active site Y122 using NotI and BlpI restriction enzyme sites. This cassette was generated by annealing 2 complementary oligonucleotides : 5'-GGCCGCAA TGCGTTATACGGAAATCCGCTTAGC-GAAAATTGCCCATGAACTGATG GCCGAT-3' (SEQ ID NO:21) and 5'-CTAGATCGGCATCAGTTCATG GGCAATTTTCGCTAAGCGGATTTCCG-TATAACGCATTGC-3' (SEQ ID NO:22). 5 nM of each oligonucleotide was combined in 1× T4 ligase buffer (New England Biolabs, Inc., Beverly, Mass.), boiled for 5 min and cooled down to room temperature. 10 µg of pEA502 were digested with NotI and XbaI using 500 U/ml each enzyme in the presence of 100 µg/ml of BSA. The digestion was performed at 37° C. for 2 hours. The digested plasmid DNA was separated by agarose gel electrophoresis and the excised band further purified using QIAEX II beads as described by the manufacturer (Qiagen, Studio City, Calif.). Ligation of the oligonucleotide cassette and the digested plasmid DNA was carried out at 20° C. for 1 hour using a 1:2 ratio of vector to insert and 40,000 U/ml of T4 ligase. Ligation products were transformed into E. coli strain ER2267 competent cells. Recombinant plasmids were checked by BlpI digestion which results in the linearization of the correct recombinant plasmids. One of the resultant correct plasmids was named pEA523.

Figure 3E:
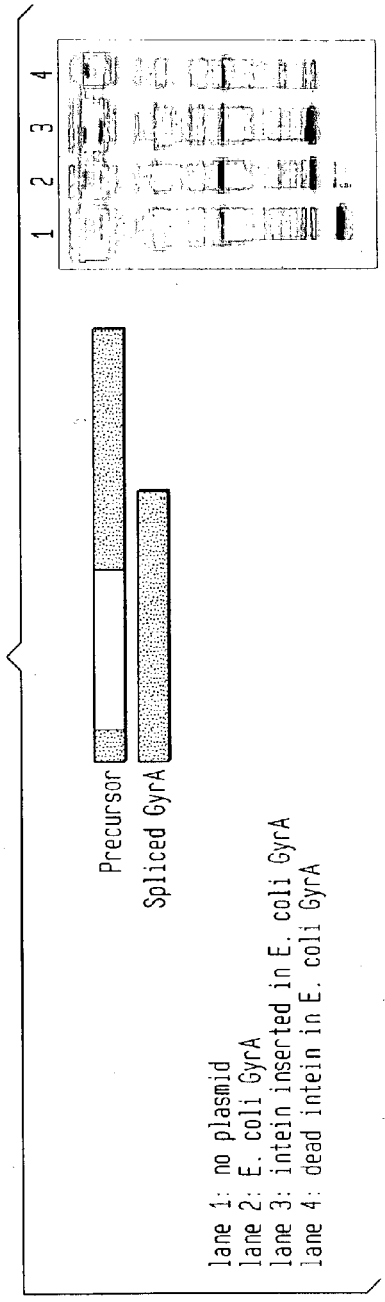
FIG. 3E is a gel indicating efficient splicing of the Mxe GyrA intein in the homologous Eco GyrA extein. The position of Eco GyrA is indicated by the solid black box and the position of the precursor comprising the Mxe GyrA intein in Eco GyrA is indicated by the black and white boxed marker with the white box indicating presence of the intein.

Fourth, the Mxe GyrA intein (IVPS) was amplified by PCR with the addition of primer derived NotI and BlpI sites using pMIP(Mxe)#4 plasmid DNA (Telenti et al., J. Bacteriol, 179:6378–6382 (1997)) under the following experimental conditions: Forward primer 5'-CGACCCGCGCG-GCCGCAATGC GTTATTGCATCACGGGAG-3' (SEQ ID NO:23) and reverse primer 5'-GCCAAAGGCGCTAAGCG-GATTTCCGTGTTGTGGCTGACGAACC CG-3' (SEQ ID NO:24) were used in a PCR mixture containing 10 U/ml Taq DNA polymerase (Promega, Madison, Wis.), 200 µM of each dNTP, 4 nM each primer and 100 ng pMIP(Mxe)#4 DNA. Amplification was carried out in a Perkin-Elmer/Cetus (Emeryville, Calif.) thermal cycler 480 at 94° C., 30 sec; 50° C., 30 sec; 72° C., 15 sec for 10 cycles. The PCR products of one 50 µl reaction and 2 µg of pEA523 were separately digested using 1000 U/ml of NotI and 300 U/ml of BlpI in the presence of 100 µg/ml of BSA. The digestion was performed at 37° C. for 2 hours. Digested PCR products and plasmid DNA were separated by agarose gel electrophoresis and the excised bands further purified using QIAEX II beads as described by the manufacturer (Qiagen, Studio City, Calif.). Ligation was carried out at 20° C. for 2 hours using a 1:3 ratio of vector to insert and 40,000 U/ml of T4 ligase (New England Biolabs, Inc., Beverly, Mass.). Ligation products were transformed into E. coli strain Top10F' (Invitrogen, Carlsbad, Calif.) competent cells. Recombinant plasmids were checked by EcoNI restriction enzyme digestion which results in the linearization of the correct recombinant plasmids. One of the resultant correct plasmids was named pEA600 and contains the in-frame insertion of the Mxe GyrA intein (IVPS) into the E. coli GyrA extein at the active site Y122 (see FIGS. 3D and 3E).

Construction of a Vector for Co-Expression of a Peptide Library and the Mxe GyrA Intein (IVPS)::E. coli GyrA Selection System As described above, the Mxe GyrA intein (IVPS) was inserted into the active site of E. coli GyrA. In this homologous context, the Mxe GyrA intein (IVPS) splices efficiently to produce active E. coli GyrA. As is detailed below, the E. coli gyrA::Mxe gyrA intein (IVPS) gene fusion described above was cloned under control of a T7 RNA polymerase promoter and introduced into E. coli, ER2726 (New England Biolabs, Inc., Beverly, Mass.). ER2726 expresses T7 RNA polymerase and has the gyrA83 mutation which makes the chromosomal gyrA gene resistant to quinoline drugs. In the presence of quinoline drugs such as ofloxacin, only splicing deficient clones can survive (see FIGS. 3B and 3C), since the spliced gyrA product is sensitive to ofloxacin in a dominant cytotoxic manner (see above).

The spectrin scaffold was cloned into EA600 as follows. First, a 30 bp DNA cassette with flanking PflMI/ApaI restriction sites was designed to be cloned into the unique PflMI/ApaI sites in pEA600 (which also contains the *E. coli* gyrA::Mxe gyrA fusion). This cassette introduced a unique SphI site in place of the lacI$^q$ gene and was synthesized by annealing 2 oligonucleotides: 5'-ATGGGCATG-CATATATATA TAGGCCTGGGCC-3' (SEQ ID NO:25) and 5'-CAGGCCTATATATAT ATGCATGCCCATTCG-3' (SEQ ID NO:26). 5 nM of each oligonucleotide was combined in 1× T4 ligase buffer (New England Biolabs, Inc. Beverly, Mass.), boiled for 5 min and cooled down to room temperature. 5 µg of pEA600 was digested using 320 U/ml of PflMI and 800 U/ml of ApaI in the presence of 100 µg/ml of BSA. The digestion was performed at 37° C. for 2 hours. The digested plasmid DNA was separated by agarose gel electrophoresis and the excised band further purified using QIAEX II beads as described by the manufacturer (Qiagen, Studio City, Calif.). Ligation was carried out at 16° C. for 1 hour using a 1:1 ratio of vector to insert and 40,000 U/ml of T4 ligase. Ligation products were transformed into *E. coli* strain XL1B (Stratagene, La Jolla, Calif.) competent cells. Recombinant plasmids were checked by SphI digestion which results in the linearization of the correct recombinant plasmids. One of the resultant correct plasmids was named pEA661.

Second, unique SgfI and sites ClaI were engineered on either side of the spectrin loop region in a spectrin encoding plasmid (Trave, et al., EMBO J. 14:4922–4931 (1995)) by site-directed silent mutagenesis using the QuickChange kit as described by the manufacturer (Stratagene, La Jolla, Calif.). The SgfI oligonucleotides were: 5'-GTTTAAGTCT-TGCTTGCGATC GCTTGGCTATGACCTGCC-3' (SEQ ID NO:27) and 5'-GGGCAGGT CATAGCCAAGCGATCG CAAGCAAGACTTAAA-3' (SEQ ID NO:28) and ClaI oligonucleotides were: 5'-GCCTGACCCCGAATTTGAATC GATTCTTGACACTGTTG-3' (SEQ ID NO:29) and 5'-CAACAGTGT CAAGAATCGATTCAA ATTCGGGGT-CAGGC-3' (SEQ ID NO:30). The resulting plasmid was called pEA670.

Third, the SgfI/ClaI mutated spectrin gene was cloned by PCR into pEA661 under the following experimental conditions. A forward primer 5'-AATGGTGCATGCAAG-GAGATGGCGCCCAAC AGTC-3' (SEQ ID NO:31) and reverse primer 5'-GCTTTGGCTAG CTTTCCTGTGTCAC-CTGCTGATCATGAACG-3' (SEQ ID NO:32) were used as described in the Expand High Fidelity PCR system (Boehringer Mannheim, Indianapolis, Ind.) in the presence of 1× buffer 2 (New England Biolabs, Beverly, Mass.) and 50 ng of pEA670 DNA. Amplification was carried out in a Perkin-Elmer/Cetus (Emeryville, Calif.) thermal cycler 480, 94° C., 30 sec; 45° C., 30 sec; 72° C., 45 sec; for 15 cycles. The PCR products of one 50 µl tube and 5 µg of pEA661 were NheI/SphI digested using 250 U/ml of each enzyme. The digestion was performed at 37° C. for 2 hours. Digested PCR products and plasmid DNA were separated by agarose gel electrophoresis and the excised bands further purified using QIAEX II beads as described by the manufacturer (Qiagen, Studio City, Calif.). Ligation was carried out at 16° C. for 1 hour using a 1:5 ratio of vector to insert and 40,000 U/ml of T4 ligase (New England Biolabs, Inc., Beverly, Mass.). Ligation products were transformed into *E. coli* strain Novablue DE3 (Novagen, Madison, Wis.) competent cells. Recombinant plasmids were checked by NheI/SphI digestion which results in the excision of the cloned insert. One of the resultant correct plasmids was named pEA671.

Fourth, the first *E. coli* gyrA PvuI site in pEA671 was eliminated by site-directed silent mutagenesis using the QuickChange kit as described by the manufacturer (Stratagene, La Jolla, Calif.) and oligonucleotides 5'-GCG-TAAAGCTCGCGACC GTGCTCATATCC-3' (SEQ ID NO:33) and 5'-GGATATGAGCACGGTC GCGAGCTT-TACGC-3' (SEQ ID NO:34), resulting in plasmid pEA681.

Figure 5A:
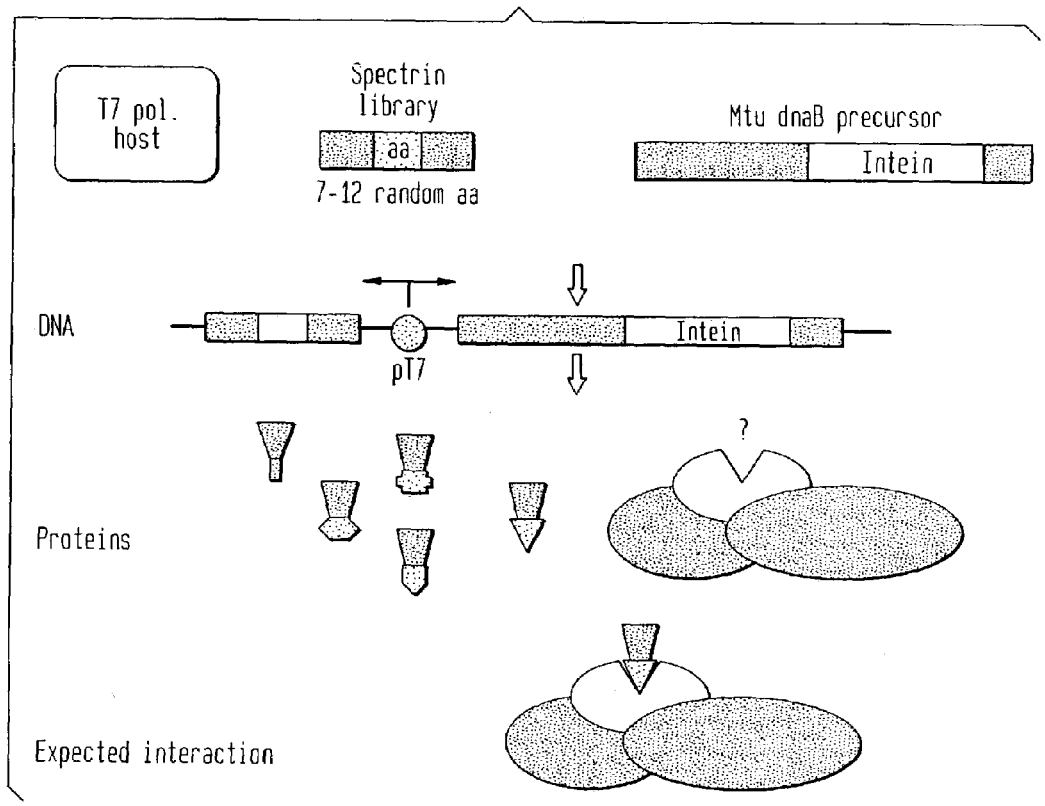
FIG. 5A is a diagram depicting the production of a combinatorial peptide library using chicken α-spectrin and the screening of these peptides for those that block Mxe GyrA helicase intein splicing. "aa" represents a portion of spectrin which can be randomized. The spectrin scaffold is represented by a trapazoid and the different amino acid sequences by various other shapes. If the spectrin binds to the precursor, splicing is blocked. The system has three components: a host cell expressing T7 RNA polymerase, the spectrin library and the intein plus GyrA gene. The latter two genes are present on a single plasmid under control of T7 RNA polymerase promoters.

Fifth, the 200 bp Acc65I/HindIII fragment from pEA681 was transferred to pEA671 replacing the Acc691/HindIII fragment of EA671. Plasmids pEA671 and pEA681 were digested in 1× buffer 2 (New England Biolabs, Inc., Beverly, Mass.) using 500 U/ml of Acc65I and 500 U/ml of HindIII (New England Biolabs, Inc., Beverly, Mass.). The digestion was performed at 37° C. for 2 hours. Digested plasmids were separated by agarose gel electrophoresis and the excised bands further purified using QIAEX II beads as described by the manufacturer (Qiagen, Studio City, Calif.). Ligation was carried out at 16° C. for 3 hours using a 1:3 ratio of vector to insert and 40,000 U/ml of T4 ligase (New England Biolabs, Inc., Beverly, Mass.). Ligation products were transformed into *E. coli* strain XL1B (Stratagene, La Jolla, Calif.) competent cells. Recombinant plasmids were checked by PvuI digestion. One of the resultant correct plasmids was named pEA682. This plasmid contains both the α-spectrin peptide library and the *E. coli* gyrA::Mxe gyrA intein-based selection system on the same plasmid, both under control of a T7 RNA polymerase promoter (FIG. 5A).

A Theoretical Screening for Peptides that Disrupt Protein Splicing of the Mxe GyrA Intein (IVPS) in *E. coli* GyrA.

Figure 5B:
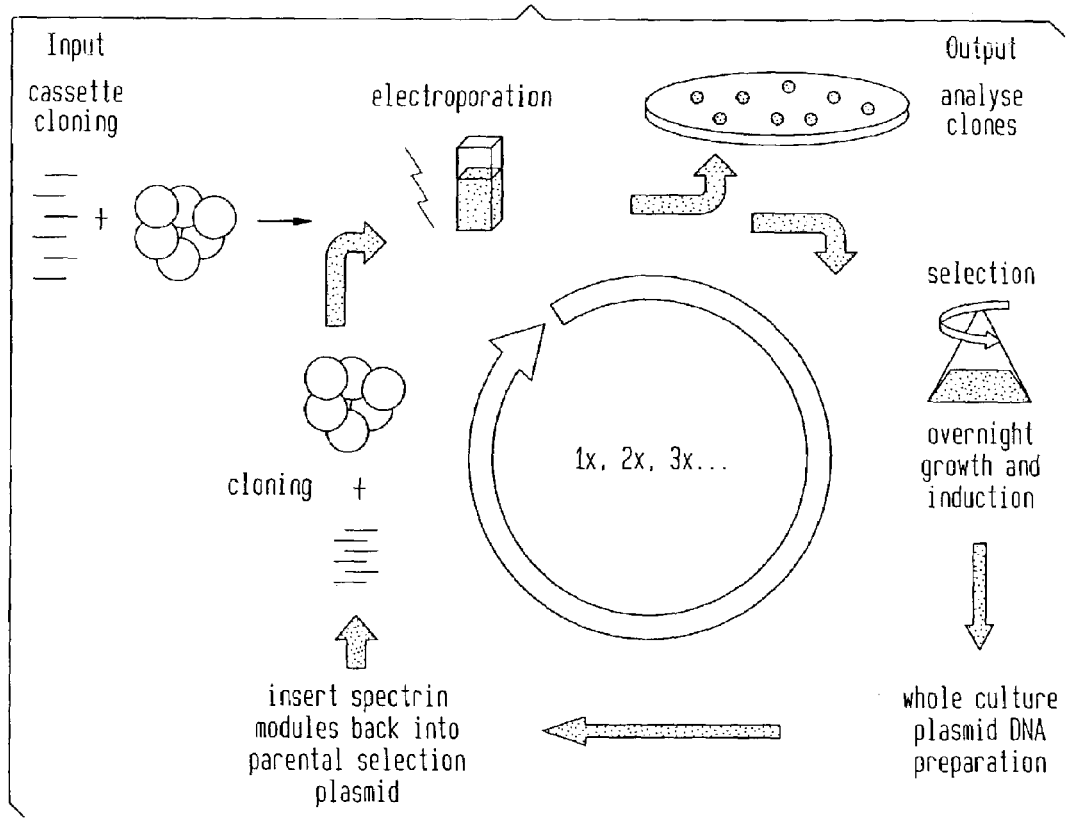
FIG. 5B is a flow diagram indicating multiple-round selection of combinatorial peptides.

In the theoretical embodiment detailed below, random peptides of 7–12 amino acids would be inserted in-frame into the loop between the 2 EF-hand motifs of α-spectrin, contained, as described above, on the same plasmid as *E. coli* gyrA::Mxe gyrA intein fusion. The resulting plasmids would be electro-transformed into strain ER2726 (New England Biolabs, Inc., Beverly, Mass.). Transformants would be selected in LB liquid growth media in the presence of ampicillin, ofloxacin (Sigma, St. Louis, Mo.) and IPTG to allow selection against the splicing proficient clones. Ampicillin selects for the presence of the plasmid and ofloxacin selects for peptides that block splicing, since the spliced *E. coli* GyrA protein would be sensitive to the drug and lead to cell death. Plasmid DNA would be isolated from selected clones and digested with SgfI and ClaI to isolate DNA fragments encoding the selected spectrin peptides. The spectrin DNA loop fragments would then be cloned back into the original selection plasmid. Iterative rounds of drug selection and "back-cloning" would be performed (FIG. 5B). Iterative screening helps enrich for agents that truly block splicing while eliminating clones that survived selection because of some other mutation or anomaly. Final selected clones would be grown individually in liquid culture and the plasmid-encoded *E. coli* GyrA specifically induced by IPTG. Crude protein cell extracts would be electrophoresed and blotted for immuno-staining. Clones in which the *E. coli* GyrA spliced product was not detected would be considered positives, i.e. clones in which splicing had been disrupted, potentially by the selected peptide.

The random peptide library would be synthesized in vitro using the following protocol, as was done in Example II. A single strand/double strand DNA hybrid cassette would be synthesized by annealing 2 oligonucleotides: 5'-TGTCAA-GAATC GATTCAAATTCGGGGTCAGGCTCTCC((W)NN)$_{7-12}$ATAGCCAAGCGA T-3' (SEQ ID NO:35) and 5'P-

CGCTTGGCTAT-3' (SEQ ID NO:36). 5 µg of oligonucleotide SEQ ID NO:35 and 3 molar equivalents of oligonucleotide SEQ ID NO:36 would be mixed together in the presence of 0.1 M NaCl in a final volume of 50 µl. The mixture would then be boiled and immediately cool down to room temperature in the same boiler. The single stranded random nucleotide part of the DNA hybrid cassette formed by annealing of the 2 oligos would be extended using 400 µM of each dNTPs and 60 U/ml of Klenow DNA polymerase (New England Biolabs, Inc., Beverly, Mass.) in a final volume of 200 µl in 1× EcoPoI buffer (New England Biolabs, Beverly, Mass.). The extension reaction would be left 20 minutes at 37° C. and further purified using QIAEX II beads as described by the manufacturer (Qiagen, Studio City, Calif.). 60 µg of pEA682 (50 µg/ml) would be digested in 1× Buffer 2 (New England Biolabs, Inc., Beverly, Mass.) using 250 U/ml of SgfI (Promega, Madison, Wis.) and 500 U/ml of BspDI (New England Biolabs, Inc., Beverly, Mass.) (an isoschizomer of ClaI) in the presence of 100 µg/ml of BSA. The digestion would be performed at 37° C. for 2 hours. Purified cassettes (50 µl) would then be digested in 1× Buffer 4 (New England Biolabs, Inc., Beverly, Mass.) using 500 U/ml of ClaI (New England Biolabs, Inc., Beverly, Mass.) in the presence of 100 µg/ml of BSA. Cassettes would be further purified using QIAEX II beads as described by the manufacturer (Qiagen, Studio City, Calif.). Digested plasmid DNA would be electrophoresed on 0.7% agarose gel and the excised bands further purified using QIAEX II beads as described by the manufacturer (Qiagen, Studio City, Calif.). Ligation would be carried out at 16° C. for 1 hour using a 1:1 ratio of vector (2 ng/µl) to insert and 1,600 U/ml of T4 ligase (New England Biolabs, Inc., Beverly, Mass.). Ligation products would then be electro-transformed into E. coli strain ER2744 (New England Biolabs, Inc., Beverly, Mass.) competent cells ($10^9$ pUC18 transformants/µg) using 1–2 µg of total ligated plasmid for each 200 µl aliquot of competent cells, at 2.5 kV/cm in a 2 mm cuvette (BIORAD, Richmond, Calif.). Cells would be allowed to recover in a shaker for 1 hour at 37° C. Recovered transformants would be inoculated at 1/100 dilution ratio into LB liquid growth media containing appropriate amounts of ofloxacin (Sigma, St. Louis, Mo.), 100 µg/ml of ampicillin and 1 mM IPTG. Transformants would be incubated overnight at 37° C. Plasmid DNA would be isolated from a 100 ml of the overnight culture using a tip100 column (QIAGEN, Studio City, Calif.), ClaI/SgfI digested as above and electrophoresed on a 4% GTG Nusieve agarose gel (FMC BioProducts, Rockland, Me.). The 57 to 72 bp spectrin loop DNA inserts (depending upon whether the peptide library contained 7 or 12 random amino acids) would be purified using QIAEX II beads as described by the manufacturer (Qiagen, Studio City, Calif.) and cloned back into SgfI/ClaI digested and purified selection plasmid as described above. This protocol would be repeated 3 times to enrich the pool of transformants for peptide clones having the most biologically active sequences against the protein splicing of the Mxe intein (IVPS). Finally selected clones would be grown individually in 10 ml LB containing 100 µg/ml ampicillin at 37° C. and induced with 1 mM IPTG for 3 hours. Crude protein cell extracts would be electrophoresed on a 10–20% gradient gel (Novex, San Diego, Calif.). The gel would then be electro-blotted for immuno-staining using anti-His tag antibodies (Sigma, St. Louis, Mo.) to detect GyrA::Mxe intein (IVPS) protein splicing products. One would expect to see the absence of spliced product. The clones would then be sequenced to determine the amino acid sequences which had been selected.

Hypothetical Screening with Agents that Inhibit Splicing

At this stage, the vector, pEA600, is amenable for screening with any type of agent that blocks splicing, using a similar screening protocol as for peptides that block splicing, described above. However, in this case, pEA600 or similar plasmids can be directly screened without having to clone the peptide library contained within the chicken α-spectrin gene as described above. The protocol would involve treating individual cultures with single or pooled agents that can enter the cell and looking for cell growth, using any means known to one skilled in the art. Agents that block splicing allow the cell to grow in the presence of ofloxacin Summary In summary, we describe the cloning of the Mxe gyrA intein gene into the E. coli gyrA extein gene for use in selecting for agents that inhibit splicing. The Mxe GyrA intein splices well in the E. coli GyrA extein, resulting in production of active E. coli GyrA protein. The E. coli GyrA extein was used with the Mxe GyrA intein because the Mle GyrA intein did not splice efficiently in E. coli in its native context and the precursor was mostly insoluble in E. coli. Because the GyrA intein and extein sequences are very similar (Telenti, et al., J. bacteriol, 179:6378–6382 (1997) and Perler, et al., Nucleic Acids Res. 27:346–347 (1999)), mixing and matching of inteins, exteins and experimental hosts resulted in an efficient model system for examining agents that modulate splicing of GyrA inteins, using exteins that have similar insertion sites and therefore similar splicing active sites as in the native context.

EXAMPLE II

A M. tuberculosis DnaB Intein-Mediated Positive Selection System

A Positive Selection System Using the Mtu DnaB Intein (IVPS) in its Native Mtu DnaB Extein in E coli: Background The hexameric E. coli helicase encoded by the dnaB gene interacts with an hexameric DnaC complex and ATP. Some DnaB mutants are dominant lethal (Bouvier and Oreglia, C. R. Acad. Sci. Hebd. Seances Acad. Sci D., 280:649–652 (1975), Maurer and Wong, J. Bacteriol 170:3682–3688 (1988), Saluja and Godson, J. Bacteriol. 177:1104–1111 (1995) and Sclafani, et al., Mol. Gen. Genet., 182:112–118 (1981)). By dominant or dominantly cytotoxic, we mean that the toxicity occurs even if homologous proteins are present which are not cytotoxic or resistant to the drug, i.e., the cytotoxic effect dominates irrespective of the presence of non-cytotoxic homologs. The mutant protein is deficient in ATP hydrolysis, helicase activity, and replication activity at the chromosomal origin of replication resulting in cell death (see FIG. 4A). Despite only moderate protein sequence identity between bacterial helicases, arginine 231 is located in a conserved motif proposed to interact directly with DnaC (Marszalek and Kaguni, J. Biol. Chem., 267:19334–19340 (1992) and Shrimankar, et al., J. Bacteriol., 174:7689–7696 (1992)). M. tuberculosis (Mtu) DnaB has a naturally occurring intein at the carboxy-terminus and an arginine at position 227 homologous to arginine 231 of E. coli DnaB (see FIG. 4D).

Figure 4C:
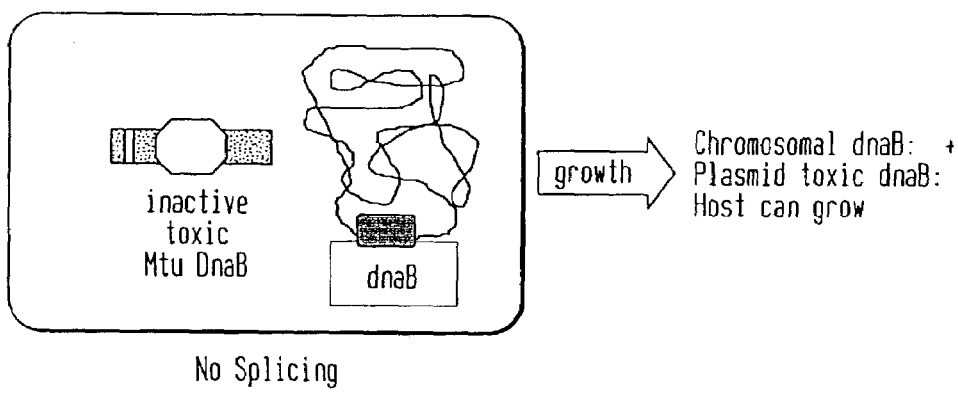
FIG. 4C is a diagram depicting a Mtu DnaB helicase intein-splicing system for the selection of agents which block intein splicing: the blocking of splicing of Mtu DnaB helicase intein out of a dominant lethal mutant Mtu DnaB helicase extein prevents the sequestration of Eco DnaC; chromosomal Eco DnaB helicase is expressed and the host grows.

We have demonstrated proficient protein splicing of the Mtu DnaB intein (IVPS) from the Mtu DnaB precursor protein in E. coli and also have shown that the R227C mutation results in dominant lethality. Therefore, a merodiploid cell containing a wild type dnaB gene and a Mtu DnaB (R227C) gene is not viable unless protein splicing can be disrupted (see FIGS. 4B and 4C). By merodiploid we mean that the cell contains an extra copy of a gene (or several genes) which has been introduced into the cell by any means known to one skilled in the art, such as transformation, infection, conjugation, plasmids, virus, phage, or by generating a transgenic strain and which may be present on either an episomal element or on the host chromosome. The co-expression of a chicken α-spectrin peptide library (as described in U.S. Pat. No. 5,834,247 supra. at Example 17) allows for the positive selection of peptides that can disrupt splicing of the *M. tuberculosis* DnaB intein (see FIG. 5A). Likewise, this system can be used to screen for any agent that inhibits splicing of the Mtu DnaB intein or any other DnaB intein in vivo or for DnaB intein mutations that block splicing.

Construction of a Positive Selection System Using the Mtu DnaB Intein (IVPS) in its Native Mtu DnaB Extein As described in detail below, the Mtu dnaB gene has been cloned by PCR under T7 RNA polymerase transcriptional control. In *E. coli*, the Mtu DnaB intein (IVPS) splices very efficiently from its natural precursor to produce the Mtu DnaB helicase. The Mtu dnaB gene has been mutagenized at position 227 from arginine to cysteine and the plasmid transformed into BL21(DE3)-Gold (Stratagene, La Jolla, Calif.). In the presence of the T7 RNA polymerase (induced by IPTG) only splicing deficient clones can survive (see FIG. 4C).

First, the Mtu dnaB gene was cloned by PCR using *M. tuberculosis* H37Ra genomic DNA under the following experimental conditions. A forward primer 5'-AGGTGAGAA TTCATGGCGGTCGTTGATGACC-3' (SEQ ID NO:37) and reverse primer 5'-TATATAAAGCTTTCATGTCACCGAGCCATGTTGGCG-3' (SEQ ID NO:38) were used as described in the Extend Long Template PCR system (Boehringer Mannheim, Indianapolis, Ind.) in the presence of 1× buffer 3 and 100 ng of *M. tuberculosis* genomic DNA. Amplification was carried out in a Perkin-Elmer/Cetus (Emeryville, Calif.) thermal cycler 480 for 2 min at 94° C. and then cycled at 45° C., 30 sec; 68° C., 2 min; 95° C., 1 min for 25 cycles. The PCR products of one 50 μl reaction and 5 μg of pET21a (Novagen, Madison, Wis.) were digested using 1000 U/ml of EcoRI and 800 U/ml of HindIII in 1× EcoRI buffer (New England Biolabs, Inc., Beverly, Mass.). The digestion was performed at 37° C. for 1 hour. Digested PCR products and plasmid DNA were separated by agarose gel electrophoresis and the excised bands further purified using QIAEX II beads as described by the manufacturer (Qiagen, Studio City, Calif.). Ligation was carried out at 16° C. for 1 hour using a 1:5 ratio of vector to insert and 40,000 U/ml of T4 ligase (New England Biolabs, Inc., Beverly, Mass.). Ligation products were transformed into *E. coli* strain Novablue DE3 (Novagen, Madison, Wis.) competent cells. Recombinant plasmids were checked by EcoRI/HindIII digestion which results in the excision of the cloned inserts. One of the resultant correct plasmids was named pEA807. The sequence of the dnaB insert was checked by DNA sequencing.

Second, the 1200 bp BglII/SgrAI fragment from pEA682 containing the spectrin-based peptide library was transferred to pEA807. Plasmids pEA682 and pEA807 were digested in 1× buffer 2 (New England Biolabs, Inc., Beverly, Mass.) using 500 U/ml of BglII and 240 U/ml of SgrAI. The digestion was performed at 37° C. for 1 hour. Digested plasmids were separated by agarose gel electrophoresis and the excised bands further purified using QIAEX II beads as described by the manufacturer (Qiagen, Studio City, Calif.). Ligation was carried out at 16° C. for 1 hour using a 1:5 ratio of vector to insert and 40,000 U/ml of T4 ligase (New England Biolabs, Inc., Beverly, Mass.). Ligation products were transformed into *E. coli* strain ER2726 (New England Biolabs, Inc., Beverly, Mass.) competent cells. Recombinant plasmids were checked by ClaI/NcoI digestion. One of the resultant correct plasmids was named pEA808.

Third, the Mtu dnaB gene was mutagenized to R227C by PCR under the following experimental conditions. A forward primer 5'-AGGTGAGAATTCATGGCGGTCGTTGATGACC-3' (SEQ ID NO:39) and reverse primer 5'-TTTCCCACGCCCGGGCaCGCCGC CACGATGACC-3' (SEQ ID NO:40) were used as described in the Extend Long Template PCR system (Boehringer Mannheim, Indianapolis, Ind.) in the presence of 1× buffer 3 (New England Biolabs, Inc., Beverly, Mass.) and 500 ng of pEA808 DNA. Amplification was carried out in a Perkin-Elmer/Cetus (Emeryville, Calif.) thermal cycler 480 for 2 min at 94° C. and then cycled at 45° C., 30 sec; 72° C., 45 sec; 95° C., 1 min for 20 cycles. The PCR products of one 50 μl reaction and 2 μg of pEA808 were digested overnight at 37° C. using 100 U/ml of EcoRI and 40 U/ml of SrfI in the 1× PCR-Script reaction buffer (Stratagene, La Jolla, Calif.). Digested PCR products and plasmid DNA were separated by agarose gel electrophoresis and the excised bands further purified using QIAEX II beads as described by the manufacturer (Qiagen, Studio City, Calif.). Ligation was carried out at 16° C. for 1 hour using a 1:1 ratio of vector to insert and 40,000 U/ml of T4 ligase (New England Biolabs, Inc., Beverly, Mass.). Ligation products were transformed into *E. coli* strain XL10-Kan (Stratagene, La Jolla, Calif.) competent cells. Recombinant plasmids were checked by NdeI/AscI. One of the resultant correct plasmids was named pEA809.

Fourth, the NotI dnaB-spectrin module was inverted on plasmid pEA809. 2 μg of pEA809 DNA was digested with 500 U/ml of NotI at 37° C. for 2 hours and digestion products split into two tubes. One tube containing 1 μg of NotI digested pEA809 was incubated further with 100 U/ml Calf Intestinal Alkaline Phosphatase (CIP, New England Biolabs, Inc., Beverly, Mass.) for 20 minutes at 37° C. Digested plasmid DNA from both tubes was separated by agarose gel electrophoresis and the excised bands further purified using QIAEX II beads as described by the manufacturer (Qiagen, Studio City, Calif.). Ligation of the vector band from the CIP treated tube and the insert band from the CIP untreated tube was carried out at 16° C. for 1 hour using a 1:1 ratio of vector to insert and 40,000 U/ml of T4 ligase (New England Biolabs, Inc., Beverly, Mass.). Ligation products were transformed into *E. coli* strain XL1-Blue (Stratagene, La Jolla, Calif.) competent cells. Recombinant plasmids were checked by SacII digest. One of the resultant correct plasmids was named pEA810.

Fifth, the $lacI^q$ gene from pEA810 was removed and replaced by a smaller DNA fragment from pBR322. pEA810 and pBR322 DNA were digested using 500 U/ml EcoRV and 500 U/ml HindIII in buffer 2 (New England Biolabs, Inc., Beverly, Mass.) at 37° C. for 2 hours. Digested plasmid DNA was separated by agarose gel electrophoresis and the excised bands further purified using QIAEX II beads as described by the manufacturer (Qiagen, Studio City, Calif.). Ligation of the pEA810 vector band and the pBR322 insert band was carried out at 16° C. for 1 hour using a 1:1 ratio of vector to insert and 40,000 U/ml of T4 ligase (New England Biolabs, Inc., Beverly, Mass.). Ligation products were transformed into *E. coli* strain XL1-Blue (Stratagene, La Jolla, Calif.) competent cells. One of the resultant correct plasmids was named pEA813.

Sixth, the first Mtu R227C dnaB AatII site of pEA813 was eliminated by site-directed silent mutagenesis using the QuickChange kit (Stratagene, La Jolla, Calif.) and oligonucleotides 5'-GCCGCCGATCCGCGACATCGTA-GATTTCGGCC -3' (SEQ ID NO:41) and reverse primer 5'-GGCCGAAATCTACGA TGTCGCGGATCGGCGGC-3' (SEQ ID NO:42) resulting in plasmid pEA832.

Seventh, the wild type intein containing Mtu DnaB gene of plasmid pEA808 was shuffled back into pEA832. pEA808 and pEA813 DNA were digested using 1× buffer 1 (New England Biolabs, Inc., Beverly, Mass.) with 500 U/ml EcoRI and 500 U/ml HindIII at 37° C. for 1 hour. Digested plasmid DNAs were separated by agarose gel electrophoresis and the excised bands further purified using QIAEX II beads as described by the manufacturer (Qiagen, Studio City, Calif.). Ligation of the pEA813 vector band and the pEA808 insert band was carried out at 16° C. for 1 hour using a 1:1 ratio of vector to insert and 40,000 U/ml of T4 ligase (New England Biolabs, Inc., Beverly, Mass.). Ligation products were transformed into E. coli strain XL1-Blue (Stratagene, La Jolla, Calif.) competent cells. One of the resultant correct plasmids was named pEA825.

Eighth, the AatII site elimination in pEA825 was performed identically as described for pEA813, resulting in plasmid pEA835.

Screening for Peptides that Disrupt the Mtu DnaB Intein (IVPS) Protein Splicing

The following is an actual experimental example demonstrating the use of this system to select for peptides that block splicing. As detailed below, random peptides of 7–12 amino-acids were inserted in-frame into the loop of the 2 EF-hand motif of α-spectrin, contained, as described above, on the same plasmid as the Mtu DnaB intein (IVPS) selection system. The resulting plasmids were electro-transformed into the T7 RNA polymerase E. coli strain ER2744 (New England Biolabs, Inc., Beverly, Mass.) (see FIGS. 5A and 5B). Transformants were selected in LB liquid growth media in the presence of ampicillin and IPTG to allow selection against the splicing proficient clones. Plasmid DNA was isolated from selected clones and digested to isolate DNA fragments encoding the selected spectrin peptides. The selected spectrin loop region DNA was cloned back into the original selection plasmid. Iterative rounds of selection and "back-cloning" were performed (FIG. 5B). After selection, the selected spectrin peptide were cloned into pEA825 (containing the non-toxic DnaB gene) for expression analysis. Final selected clones were grown individually in liquid culture and the plasmid-encoded Mtu dnaB gene specifically induced by IPTG. Crude protein cell extracts were electrophoresed and blotted for immunostaining. Clones in which the Mtu DnaB spliced product was not detected were considered positives, i.e. clones in which splicing had been disrupted, potentially by a selected peptide.

Figure 5C:
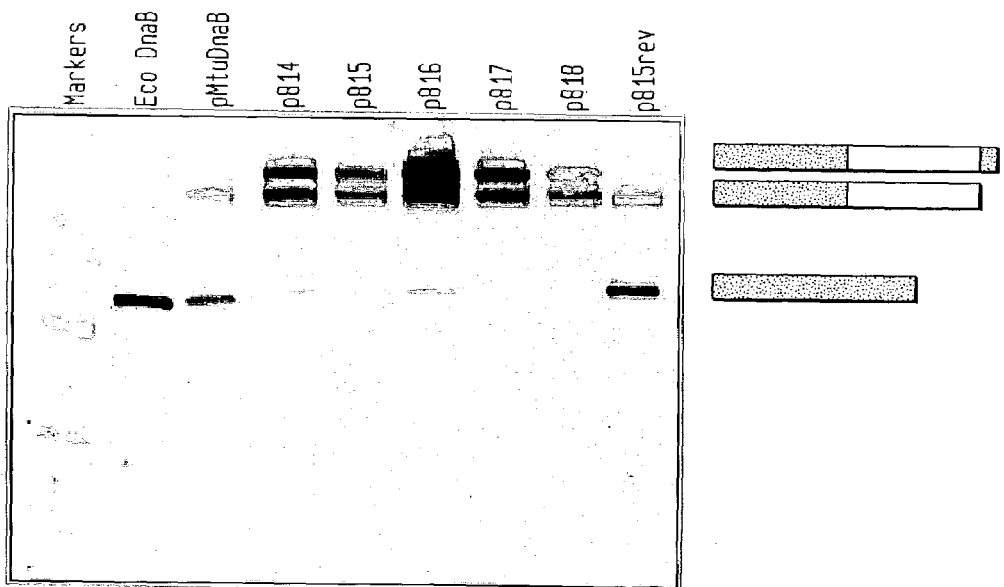
FIG. 5C is a gel indicating that peptides p814–818 (SEQ ID NO:5, SEQ ID NO:6, SEQ ID NO:7, SEQ ID NO:8, SEQ ID NO:9 and SEQ ID NO:10) block splicing of Mtu DnaB in E.coli. This is a Western block using anti-T7 tag antibody to detect the T7 tag at the N-terminus of each DnaB protein. In p815rev, the selected blocking peptide sequence in α-spectrin has been replaced with the wild type spectrin sequence to demonstrate that inhibition of splicing is due to the selected peptide sequence. The bands and markers on the right represent the precursor, a putative C-terminal cleavage product and the spliced DnaB exteins, respectively from top to bottom of the Western Blot. Size markers are in lane M.

The random peptide library was synthesized in vitro using the following protocol. A single strand/double strand DNA hybrid cassette was synthesized by annealing of 2 oligonucleotides: 5'-TGTCAAGAATCGATTCAAAT-TCGGGGTC AGGCTCTCC((W)NN)$_{7-12}$ ATAGC-CAAGCGATCGCAGGCAGCTTTT AAAGCCCTGATGGTTCAGACGT-3' (SEQ ID NO:43) and 5'P-CTGAACCATCAGGGC-3' (SEQ ID NO:44). 5 μg of oligonucleotide SEQ ID NO:43 and 3 molar equivalents of oligonucleotide SEQ ID NO:44 were mixed together in the presence of 0.1 M NaCl in a final volume of 50 μl. The mixture was boiled and immediately cooled down to room temperature in the same boiler. The single strand random nucleotide part of the DNA hybrid cassette formed by annealing of the 2 oligos was extended using 400 μM of each dNTPs and 60 U/ml of Klenow DNA polymerase (New England Biolabs, Inc., Beverly, Mass.) in a final volume of 200 μl in 1× EcoPol buffer (New England Biolabs, Inc., Beverly, Mass.). The extension reaction was incubated 20 minutes at 37° C. and further purified using QIAEX II beads as described by the manufacturer (Qiagen, Study City, Calif.). 60 μg of pEA832 (50 μg/ml) were digested in 1× Buffer 4 (New England Biolabs, Inc., Beverly, Mass.) using 400 U/ml of AatII (New England Biolabs, Inc., Beverly, Mass.) and 500 U/ml of ClaI (New England Biolabs, Inc., Beverly, Mass.) in the presence of 100 μg/ml of BSA. The digestion was performed at 37° C. for 2 hours. Synthesized random cassettes (20 μg/ml) were digested in 1× Buffer 4 (New England Biolabs, Inc., Beverly, Mass.) using 500 U/ml of ClaI (New England Biolabs, Inc., Beverly, Mass.) in the presence of 100 μg/ml of BSA. Cassettes were further purified using QIAEX II beads as described by the manufacturer (Qiagen, Studio City, Calif.). Digested plasmid DNA was electrophoresed on a 0.7% agarose gel and the excised bands further purified using QIAEX II beads as described by the manufacturer (Qiagen, Studio City, Calif.). Ligation was carried out at 16° C. for 1 hour using a 1:1 ratio of vector (2 ng/μl) to insert and 1,600 U/ml of T4 ligase (New England Biolabs, Inc., Beverly, Mass.). Ligation products were electro-transformed into E. coli strain ER2744 (New England Biolabs, Inc., Beverly, Mass.) competent cells (competency of 1×10$^9$ pEA835 transformants/μg) using 2 μg of total ligation product for each 200 μl aliquot of competent cells, at 2.5 kV/cm in a 2 mm cuvette (BIO-RAD, Richmond, Calif.). Cells were allowed to recover in a shaker for 1 hour at 37° C. Recovered transformants were inoculated at 1/100 dilution into LB liquid growth media containing 100 μg/ml of ampicillin and 1 mM IPTG. Transformants were incubated overnight at 30° C. Plasmid DNA was isolated from the overnight culture using tip100 columns (QIAGEN, Studio City, Calif.)), AatII/ClaI digested as above and electrophoresed on a 4% GTG Nusieve agarose gel (FMC BioProducts, Rockland, Me.). The 57 to 72 bp spectrin loop DNA inserts were purified using QIAEX II beads as described by the manufacturer (Qiagen, Studio City, Calif.) and cloned back into AatII/ClaI digested and purified selection plasmid (pEA832) as described above. This protocol was repeated 3 times to enrich the pool of transformants for peptide clones having the most biologically active sequences against the protein splicing of the Mtu DnaB intein (IVPS). Finally selected spectrin modules were cloned into a pEA832 homologous plasmid containing the wild type Mtu dnaB gene (pEA825) and grown individually in 10 ml LB containing 100 μg/ml ampicillin at 37° C. and induced with 1 mM IPTG for 3 hours. Crude protein cell extracts were electrophoresed on a 10–20% gradient gel (Novex, San Diego, Calif.). The gel was further electroblotted for immuno-staining using anti-T7 tag antibodies (Novagen, Madison, Wis.) to detect Mtu DnaB protein splicing products (FIG. 5C). Lane Eco DnaB contains extracts of T7-tagged E. coli DnaB without the intein. pMtuDnaB contains extracts from a clone expressing only Mtu DnaB. Lanes p814, p815, p816, p817, and p818 contain extracts of the clones pEA814, pEA815, pEA816, pEA817, and pEA818, respectively, encoding peptides selected for inhibition of splicing. To demonstrate that the inhibition of splicing was due to the peptide inserted into the chicken α-spectrin loop, the selected sequence of pEA818 was replaced with the spectrin sequence, DLPMVEE (SEQ ID NO:10) to generate clone pEA818rev, and extracts loaded on lane p818rev. Splicing of pEA818rev occurred as efficiently as with the pMtu DnaB clone that expresses the wild-type spectrin protein. Note that in the absence of splicing, much of the DnaB precursor undergoes cleavage at the intein C-terminal splice junction.

The sequence of the inserted peptides in these clones is as follows:

| pEA814 | TVQSTKR | (SEQ ID NQ:5) |
| pEA815 | RPAPRPL | (SEQ ID NO:6) |
| pEA816 | PTARTYE | (SEQ ID NO:7) |
| pEA817 | PTRPTAPPLNFS | (SEQ ID NO:8) |
| pEA818 | HPNPHPTLSGQR | (SEQ ID NO:9) |
| pEA818rev | DLPMVEE | (SEQ ID NO:10) |

We have thus demonstrated that this system can be used to select for peptides that block splicing of the Mtu DnaB intein. This system is amenable to selection of any modulators of splicing of the Mtu DnaB intein or other DnaB inteins, as long as the agent can enter a cell.

EXAMPLE III

In Vivo Control of Protein Splicing for Chemotherapeutic Purposes or to Make Controllable Gene Knockouts The selection and screening systems described for selection of agents that modulate protein splicing can also be applied to intein-less versions of the extein gene to select for agents that inhibit or activate the extein gene product. All of the selection and screening systems described in this patent are based on the activity or inactivity of the extein portion of the precursor. If one deletes the intein from the intein-containing gene by methods known to one skilled in the art, then one can select for agents that block or activate extein activity also using the methods described for inhibiting or activating splicing of the intein containing precursor, since these latter methods involve assaying extein function. For example, if one deletes the intein from the Mtu DnaB gene by methods known to one skilled in the art, then one can select for agents that block activity of the cytotoxic Mtu DnaB protein using the methods described for inhibiting splicing of the DnaB intein. *M. tuberculosis* can then be attacked using a cocktail of two agents that block activity of the essential DnaB protein, making it more difficult for the organism to develop resistance to these agents.

We have previously described the insertion of a CIVPS or IVPS into a foreign gene. In these cases, protein splicing could be controlled by temperature, mutation, pH, photo-activated blocking groups, phosphorylation or peptides (Comb, et al., U.S. Pat. No. 5,834,247 and Comb, et al., U.S. Pat. No. 5,496,714). In this Example we describe a general method for selecting specific protein splicing inhibiting or activating agents that are capable of controlling protein splicing in vivo or in vitro. The methods are equally applicable to genetic selection systems or reporter systems. By genetic selection, we mean, in this Example, that viability or growth rate of the test organism is monitored during the experiment, while a reporter system in this Example refers to the monitoring of a marker, such as color detection, fluorescence, phenotype, etc., rather than cell viability. Genetic selection or reporter systems are used to identify agents that can either disrupt or catalyze protein splicing of a given intein, depending on the context of the experiment. Any genetic selection or reporter system known to one skilled in the art can be used to isolate agents which disrupt or catalyze protein splicing. This strategy is equally applicable to any intein present in a foreign context or in its native or homologous context (e.g., the insertion of an intein at the same position in an homologous extein). However, use of the native extein is preferable because it best represents the enzyme target of the intein. If the native precursor does not express well or splice well in the experimental host organism, then the intein can be inserted into the same site in that host organism's homolog of the native extein or in another extein homolog with desired properties for testing, using any method known to one skilled in the art or described in the previous Examples. This method of finding agents that modulate splicing is applicable to any host, as long as the protein splicing precursor is operably linked to the appropriate control signals for transcription and translation in that host. As the target organism may not be an easy experimental model for identifying agents that modulate protein splicing, the agent may first be identified in a model system and then tested in the final target organism. This strategy is summarized in FIG. 8.

Experiments involving inhibition of splicing start with a precursor that contains a fully active intein that may or may not be controllable. The goal of this experiment is to find agents that can be used to control splicing of this intein. In experiments involving activation of splicing, a CIVPS (controllable intein) or an inactive intein is required, as the goal is to find agents that activate the previously inactive intein. The intein may be inactivated by any means known to one skilled in the art, such as temperature sensitive inteins, inteins with mutations in amino acids known to be involved in catalysis that slow down or block splicing (including the conserved amino acids at both splice junctions and in intein Block B, (Perler, Nucleic Acids Res. 25:'087–1093 (1997), Pietrokovski, Protein Sci., 3:2340–2350 (1994)) inteins which have been randomly mutated and selected for inhibition or blockage of splicing.

Figure 8:
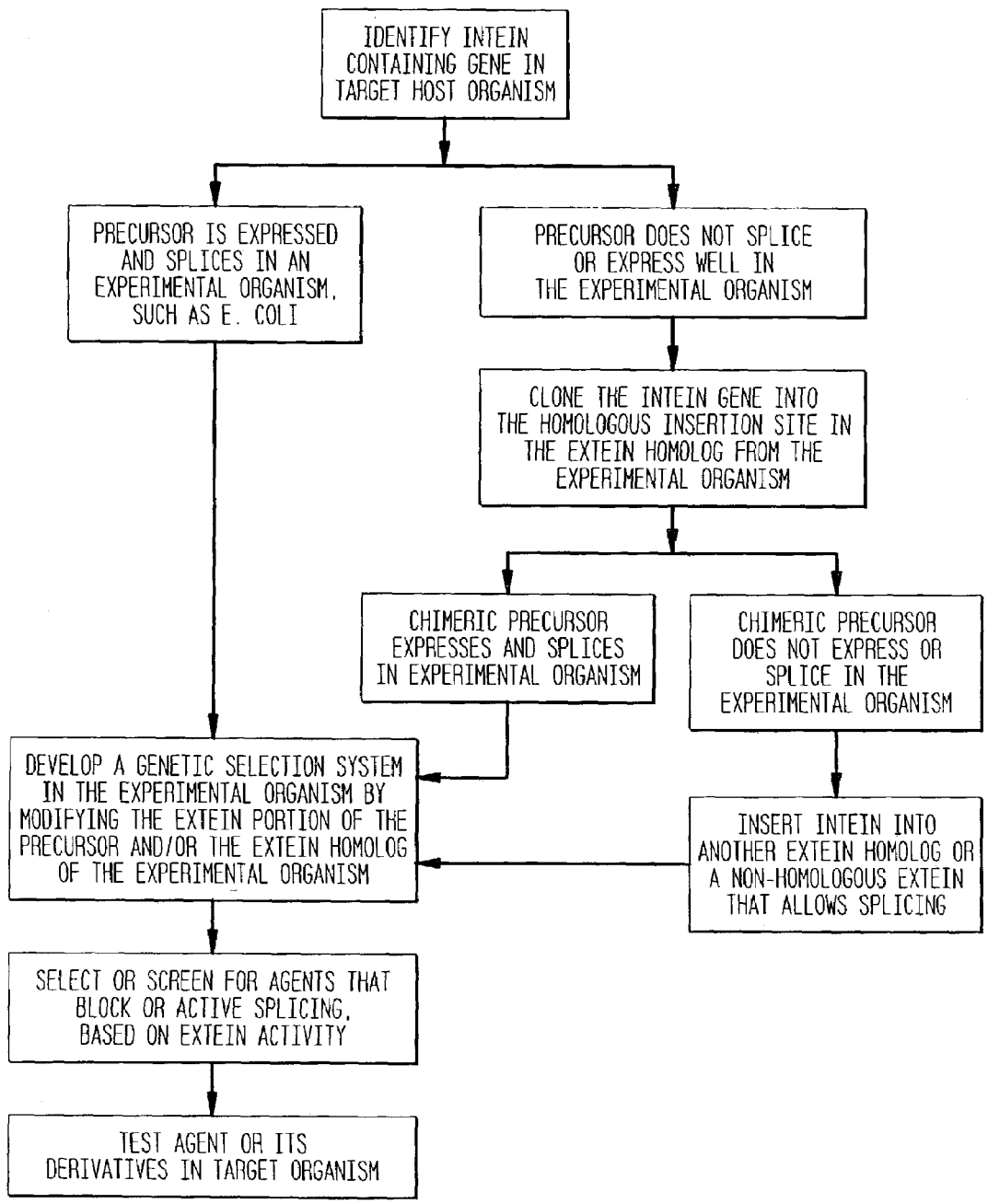
FIG. 8 is a flow chart for choosing native precursors, homologous exteins or heterologous exteins to develop a selection or reporter system for testing agents that inhibit or activate splicing of an intein.

A positive selection system is preferred. In general, a positive selection system consists of a gene that is detrimental to a host organism depending on the growth media or the host strain genetic background. The gene product is static or lethal for the cell, killing the host or preventing growth unless the gene product is inactivated. The gene product may be directly cytotoxic to the host in a dominant manner, as in the DnaB example (Example II) or it may be dominantly cytotoxic in response to a drug which the chromosomal copy of the gene is resistant to, as in the GyrA example (Example I). By dominant or dominantly cytotoxic, we mean that the toxicity occurs even if homologous proteins are present which are not cytotoxic or resistant to the drug, i.e., the cytotoxic effect dominates irrespective of the presence of non-cytotoxic homologs. In the context of a protein splicing inhibition system, positive selection involves a system that allows selection against the splicing of an IVPS or intein. If splicing occurs, the cytotoxic extein protein will be active and kill the cell or inhibit growth; if splicing is disrupted, the cytotoxic extein protein will be inactive and cells will grow. Cell growth can be monitored by any means known to one skilled in the art, including, but not limited to obervation of a colony on solid media, optical density, monitoring of fluorescent reporters of cell growth such as green fluorescent protein of luciferase activity. The extein gene may be an unrelated reporter system or the natural extein of the intein (either using the natural precursor or inserting the intein into a homologous extein context) (FIG. 8). In this context, selection systems have the advantage that only agents that inhibit splicing allow cell growth and are thus easily found amongst the background of agents that have no effect on splicing or are directly toxic to the cell. If the agents to be tested are also expressed in the host cell, then one examines the colonies that survive on the plate. If the agent to be tested is not expressed in the host cell, but is instead added to the media, then aliquots of host cells must be arrayed for testing with individual agents or pools of agents in any number of devices, such as microtiter dishes. In such cases, cell growth may be more easily measured if the cells expres a protein that leads to fluorescence, such as green fluorescent protein or luciferase.

When selecting for agents that activate splicing, the intein is already present or is inserted into a gene whose protein product is required for cell growth. In the absence of splicing, the cell fails to grow or dies. In order to practically employ this selection system, a second gene is present which can rescue the cell in the absence of splicing. This second copy of the gene should be controllable, by methods such as a temperature sensitivity or controllable promoters, to allow cell growth until the agent which activates splicing is applied or induced in the cell. The cells are treated with the splicing activator and then moved to the nonpermissive condition for activity of the second gene product that does not contain the intein or expression of this gene is turned off. Cell growth will then require splicing since the second gene product lacking the intein is no longer active.

Another method for identifying agents that modify protein splicing involves screening rather than genetic selection. Screening systems employ reporter genes whose products can be readily assayed, but do not necessarily affect cell growth. Many reporter systems are known, such as the blue/white β-galactosidase screening system. β-galactosidase acts on X-gal, for example, to generate a blue color; in the absence of β-galactosidase activity, the X-gal remains uncolored or 'white'. Other reporters include those described in Burns and Beacham, Gene, 27:323–325 (1984) and Mechulam, et al., J. Bacteriol., 163:787–791 (1985). One can use native precursors if reporter systems are available for those extein genes or the intein can be cloned into the reporter gene (β-galactosidase in this Example) (see for example, Belfort, U.S. Pat. No. 5,795,731 and Comb, et al., U.S. Pat. No. 5,834,247). Agents that inhibit splicing of an otherwise active intein will block reporter protein functions, such as β-galactosidase action on X-gal, resulting in white instead of blue clones. Agents that activate splicing of an otherwise inactive or slowly acting intein restore reporter protein functions, resulting in blue clones using the β-galactosidase system as an example. If the agents to be tested are also expressed in the host cell, then one examines the colonies that survive on the plate. If the agent to be tested is not expressed in the host cell, but is instead added to the media, then aliquots of host cells must be arrayed for testing with individual agents or pools of agents in any number of devices, such as microtiter dishes. Unlike selection, all cells grow in reporter systems and one must determine whether the read out is positive or negative for each colony or microculture.

Previous Examples have described genetic selection systems based on the pheS non-homologous selection system and the gyrA and dnaB intein/extein systems. This Example describes how one would screen for agents that modulate splicing using any selection or reporter system. Note that the selection or screening systems may not have been originally identified in the organism containing the intein. However, if a selection or screening system has been described for the extein homolog, it can be adapted to the intein containing homolog. As in the case of DnaB, the same mutation can be made in the intein containing homolog to generate a selectable phenotype for the intein containing extein gene. As in the case of GyrA, the screening system can involve a chromosomal mutation that leaves the host resistant to a drug; all that need be done is to show that the intein containing homolog is also sensitive to the drug.

Iterative screening (FIG. 5B) provides a method of identifying lead compounds and reducing background and can be used in any of the schemes described below. Iterative screening involves repeated cycles of testing of the agent on fresh extein genes. It helps insure that the agent is not acting on a mutated extein, which could also be a by-product of screening.

Positive Selection Systems for Inhibition or Activation of Protein Splicing of an Intein in its Natural Precursor or an Extein Homolog In this case, the intein of interest is naturally found in a target gene which can naturally serve as a selectable marker or reporter or which can be converted into a selectable marker or reporter. Initial experiments may be performed in the target organism or an experimentally more amenable model host such as bacteria, E. coli, yeast, mammalian cells, insect cells, etc. The decision as to whether to use the natural splicing precursor to select for agents that block splicing or to first insert the intein gene into a homologous extein gene from a model organism depends on the similarity amongst the extein genes, the ability of the natural precursor or recombinant precursors to express in the model hosts used for selection or screening, and the ability of each precursor to splice in the model hosts. (FIG. 8) These parameters will have to be experimentally determined, although the more similar the extein sequences, the more likely that splicing will work in the homologous extein protein from the model organism. Sequence comparison will indicate the appropriate homologous intein insertion site in the homologous extein gene from the model organism.

Next, one has to determine by a literature search whether any genetic selection systems or screens are available for the target extein in any organism and whether the extein gene is essential for cell growth in any organism. If the target gene is essential, but no genetic selection or screens are available, it can be mutagenize directly or in model systems to attempt to generate a selection or reporter system. If the target gene product is essential to the cell, under defined conditions, the host gene can be either knocked out and replaced by a controllable copy of the gene or mutated to generate a temperature sensitive activity. The intein containing gene must the produce an active product when the host gene homolog is inactivated. A temperature sensitive phenotype can easily be generated by random or rational mutation by one skilled in the art. Once a selection system has been identified and the best splicing precursor has been determined (selecting from the naturally occurring precursor, or after inserting the intein into the homologous extein from the target or selection organism), testing for agents that block splicing can begin in either a model organism or the target organism, depending on ease of use. Some of the possible schemes for identifying agents that block or activate splicing are shown in FIG. 9.

Scheme 1 is a method for selecting for agents that inhibit splicing. The selection system involves a dominant cytotoxic phenotype in response to a drug. By dominant cytotoxic we mean that the spliced product is toxic to the cell irrespective of expression of a resistant copy of the extein gene. The GyrA system described in Example I is an example of this type of scheme. The selection host organism contains a chromosomal copy of the extein gene that is resistant to the drug and allows growth of the organism in the presence of the drug. First, a merodiploid is made containing a gene which is sensitive to the drug and contains the intein, and a gene which is resistant to the drug and does not contain an intein. Second, the host containing the resistant extein gene and the intein containing sensitive extein gene is then treated with agents that can enter the cell or by induction of expression of agents within the cell. Finally, the selection drug is added to the cells. If the intein splices, the drug sensitive target protein kills the cell or inhibits growth when the drug is present. If any agent blocks splicing, no drug sensitive extein protein is made and the organism grows. Usually, one tests a library of compounds of any type, rather than a single agent, and one uses small cultures, as in microtiter dishes, for example. Any type of agent can be used, as long as it can enter the cell. Alternatively, the agent can be cloned and expressed in the target cell and clones can be tested for growth on plates or in liquid media. Expression of combinatorial peptide libraries would be an example of such an agent that is expressed in the cell.

Scheme 2 is a second method for selecting for agents that inhibit splicing. The selection system involves a dominant lethal phenotype in the absence of exogenous drug treatment that is inherent in the intein containing extein protein or can be introduced into the extein protein. The DnaB system described in Example II exemplifies this type of system. The selection host organism contains a wild type gene that is not toxic to the cell and allows growth of the organism. First, a mero-diplid is made containing a gene which is toxic to the cell, but contains an intein and an intein-less extein gene which is not toxic. Next, this host is treated with agents that can enter the cell before the cytotoxic precursor gene is expressed. Finally, expression of the intein containing cytotoxic extein gene is induced. If the intein splices, the cytotoxic target protein kills the cell or inhibits growth. If any agent blocks splicing, no cytotoxic target protein is made and the organism grows. Usually, one tests a library of compounds of any type, rather than a single agent, and one uses small cultures, as in microtiter dishes, for example. Any type of agent can be used, as long as it can enter the cell. Alternatively, the agent can be cloned and expressed in the target cell and clones can be tested for growth on plates or in liquid media. Expression of combinatorial peptide libraries would be an example of such an agent that is expressed in the cell.

Scheme 3 selects agents that inhibit splicing of an essential gene. In this case, the chromosomal copy of the gene, or its equivalent, is either temperature sensitive, sensitive to a drug in a recessive manor, or under some type of expression control. Alternatively, the chromosomal copy of the extein gene is inactivated or knocked out. The cells can grow under conditions where the gene product is not needed. The cells are then shifted to conditions which require the extein protein for survival. An example of this type of extein is a metabolic enzyme. When cells are grown in rich media, they can grow. However, when cells are grown in minimal media or media lacking the downstream product of the extein blocked metabolic pathway, the cells fail to grown. The intein containing target gene is not temperature sensitive or is resistant to the drug. If splicing occurs under non-permissive conditions for the chromosomal extein homolog, then the cells live. This system requires assay of cell growth in isolated containers, such as microtiter dish wells, for example. If the agent blocks splicing, then the cells will not grow under non-permissive conditions for activity of the intein-less copy of the extein protein. Cell growth can be determined by any means known to one skilled in the art, including, but not limited to measuring optical density or presence of a fluorophore generated in the cell. First an experimental host must be found that contains a controllable copy of the extein gene or its equivalent. It is propagated under permissive conditions for expression of active intein-less extein protein. Second, this host is transformed with a vector containing a wild type extein gene or extein homolog gene containing the intein. Third, merodiploid cells containing the intein-plus and intein-minus copies of the extein gene, or its equivalent, are treated with agents to block splicing and are also shifted to non-permissive conditions for activity of the intein-less extein protein. This may involve a shift to a temperature at which the intein-minus protein is inactive, removal of inducers for expression of the intein-minus shifting to different media, or addition of a drug which inactivates the intein-minus protein. If splicing occurs, the cells will continue to grow using the intein-plus gene product. However, if the agent inhibits splicing, products of both copies of the gene are inactivated and the cells die. Alternatively, the agent can be cloned and expressed in the target cell. However, in this case, each clone must be copied or replica plated to maintain a living copy of the library and a copy to be tested for inhibition of splicing. Expression of combinatorial peptide libraries would be an example of such an agent that is expressed in the cell.

Schemes 4–6 are methods of selecting for agents that activate splicing rather than inhibit it. The precursor contains an inactive intein which is introduced into the cell on any type of vector. The agent(s) may be added individually or in pools to isolated cultures. Alternatively, the agent can be cloned and expressed in the target cell. However, in this latter case, each clone must be copied or replica plated to maintain a living copy of the library and a copy to be tested for activation of splicing. Expression of combinatorial peptide libraries would be an example of such an agent that is expressed in the cell.

Scheme 4 is identical to scheme 1. In the presence of the drug, an agent that activates splicing kills the host since the intein-plus drug sensitive copy of the gene is active and dominantly cytotoxic. One assays for the absence of growth in isolated cultures, such as microtiter dish wells, for example.

Scheme 5 is similar to scheme 1. An agent that activates splicing kills the host since the dominantly cytotoxic extein is active after splicing of the intein, irrespective of the presence of the wild type extein protein derived from the intein-minus gene. One assays for the absence of growth in isolated cultures, such as microtiter dish wells, for example.

Scheme 6 is similar to scheme 3, except that the selection system requires expression of the spliced target gene for cell growth and selects for agents that activate splicing. In this type of system, the intein-minus copy of the target extein gene, or its equivalent, is either temperature sensitive, sensitive to a drug in a recessive manor, or under some type of expression control. Alternatively, the chromosomal copy of the extein gene is inactivated or knocked out. The cells can grow under conditions where the gene product is not needed. The cells are then shifted to conditions which require the extein protein for survival. An example of this type of extein is a metabolic enzyme. When cells are grown in rich media, they can grown. However, when cells are grown in minimal media or media lacking the downstream product of the extein blocked metabolic pathway, the cells fail to grow. The intein containing target gene is not temperature sensitive or is resistant to the drug. The target gene containing the intein is introduced into the cell by any means known to one skilled in the art. In this case, the intein has been modified so that it can not splice under the assay conditions. The host copy of the gene is expressed in an active form under permissive conditions (permissive temperature, in the absence of drug, rich media under permissive expression conditions, etc.), allowing the cells to grow. The intein-plus copy of the target extein gene, containing the inactive intein, is introduced into the cell. After expression of the intein precursor is established, agents are added externally or peptide libraries are expressed internally to induce splicing. After allowing the agent to activate splicing, the cells are shifted to the non-permissive condition (non-permissive temperature, in the presence of drug, minimal media under non-permissive expression conditions, etc.). The only cells that can grow are those in which splicing activity has been restored by the agent. If an external agent is to be tested, then the agent is added to cells in isolated containers, such as microtiter dish wells. Alternatively, the agent can be cloned and expressed in the target cell. In this case, the library of agents can be directly tested for cell viability on plates. Expression of combinatorial peptide libraries would be an example of such an agent that is expressed in the cell.

Reporter Systems for Inhibition or Activation of Protein Splicing of an Intein in its Natural Precursor or an Extein Homolog Any extein that can be converted into a tractable phenotype can be used in a reporter system screen. This type of system requires the ability to differentiate between active and inactive extein by any direct or indirect means. Once the reporter system is available, the intein containing gene is introduced into the cell by any method known to one skilled in the art and agents that inhibit splicing are added or induced as above. Alternatively, an inactive intein is introduced into a cell and agents that activate it are added or induced as above. One then examines individual clones and determines whether the extein is active or not.

Systems for Inhibition or Activation of Protein Splicing of an Intein in an Unrelated Extein Context The scenario for this method of identifying agents that inhibit or activate splicing is the same as schemes described above, except that the intein is placed in an unrelated extein. However, one must first determine that the intein splices in the non-homologous extein (FIG. 8). To improve the probability that an intein will splice in a non-homologous foreign context, the intein insertion site should be as similar to the natural extein sequence as possible for at least 1 and up to 5 or more extein residues. If the intein is inserted into a nonessential region of the target protein, one could possibly modify the sequence of the target protein at the intein insertion site to be the same as the native extein sequence of that intein. The intein must be cloned prior to a Ser, Thr or Cys with the amino acid naturally following the intein being the best choice or the Ser, Thr or Cys codon must be inserted into the extein along with the intein sequence. To improve folding, surface locations on the protein would be preferable since they are more likely to allow the extein to fold independently of the intein. If the structure of the target protein is unknown, protease sensitive sites on the target protein should be good positions to insert the intein.

Since splicing can be sequence dependent, it is optimal to experimentally identify agents that modify splicing in the same target protein that one wants to finally control. However, agents could possibly also control splicing of that intein in any extein. New exteins may have to be treated experimentally.

Controllable Knockouts

Once an agent has been found which can inhibit or activate splicing, the homologous extein gene in the target organism is replaced by the homologous gene containing the intein by methods known to one skilled in the art. for example, this may be performed in a one step process by inserting the intein-containing gene directly into the chromosomal copy of the extein gene by homologous recombination. Alternatively, the intein containing gene is introduced into the organism and the non-intein containing homolog is inactivated either concurrently or separately and in any order of event. Once the only copy of the active extein gene contains a intein, gene function can be inhibited if the organism is treated with an agent that blocks splicing. On the other hand, if a splicing impaired intein is used, gene function can be activated if the organism is treated with an agent that activates splicing. The agents and splicing can be modulated at any time during the development and life of the organism by addition or removal of the splicing activating or inhibiting agent. For example, a gene for mouse embryogenesis can be replaced by an intein containing gene homolog and the product of that gene can be activated or inactivated at various times to determine when the gene product is required and if it is required during multiple stages of development or growth. In a second example, a gene product thought to be required for passage through a specific stage of the cell cycle could be replaced with an intein containing copy that would allow study of exactly when the gene product is required or to synchronize the culture by arresting all cells at the same point in the cell cycle to study the effect of any agent, etc., on a synchronized culture of cells.

Use of Controllable Inteins (CIVPS) in Therapeutics

Several options can be envisioned for the use of controllable splicing to deliver active proteins at specific times or to specific places. In many instances, therapeutic drugs can be cytotoxic to the host and would be best if only active at the target site. For example, chemotherapy drugs are often generally cytotoxic and adverse reactions in normal cells could be eliminated if the drug could be specifically activated in the tumor. If one has a drug that is at least partially proteinacious, an intein that can be activated or inhibited by a second agent, as described above, could be inserted into the protein portion of the therapeutic agent. The drug is then administered systemically in an inactive form. The drug could then be specifically activated in the tumor or target organ by (1) injecting the activating agent into the tumor, (2) exposing the tumor to laser treatment to increase the temperature of the tumor and thus induce splicing of a temperature sensitive intein, (3) use gene therapy to target the inactive cytotoxic precursor to the tumor cells and then add the splicing activator systemically or (4) use gene therapy to target the activating peptide to the tumor and add the inactive intein containing drug systemically. In the Examples described above, the inactive cytotoxic precursor or the activating peptide, respectively, could be transformed systemically with a vector that is not tissue or cell specific, and only expressed in specific target cells by operably linking these genes to tissue specific promoters.

EXAMPLE IV

Methods for Generating Temperature Controllabel Inteins

Figure 11:
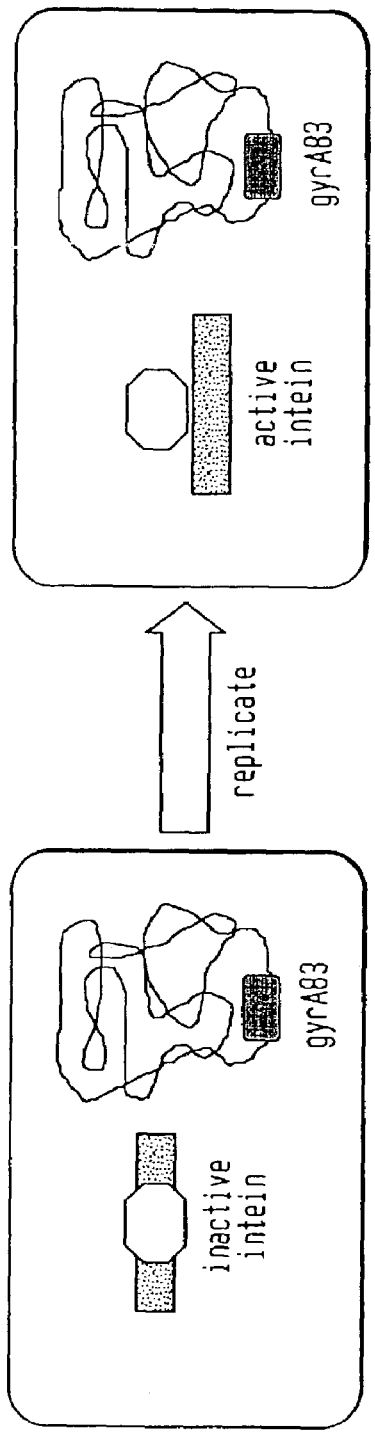
FIG. 11 depicts the selection scheme based on the GyrA selection described in Example I in which the presence of a drug kills cells where the intein has spliced. Clones that do not splice at Temperature 1 grow, while replica plated clones that splice at lower Temperature 2 do not grow.

The methods used for identifying agents that inhibit or activate splicing can also be used to identify inteins that are active at one temperature and inactive at a second temperature (referred to as temperature sensitive inteins). Instead of adding an external agent or expressing an internal agent, the intein is randomly mutated by any method known to one skilled in the art, such as error prone polymerase chain reaction (FIG. 10) or use of combinatorial DNA sequences at specific regions in the intein. Alternatively, one can specifically mutate residues thought to function in or assist the chemical reactions, such as the C-terminal splice junction residues, the intein N-terminus, the intein penultimate residue, the residues in intein Block B (Perler, *Nucleic Acids Res.*, 25:1087–1093 (1997); Perler, *Nucleaic Acids Res.*, 27:346–247 (1999); Pietrokovski, supra), residues proximal to the intein active site as determined crytallographically (Duan, et al., *Cell*, 89:555–564 (1997); Klabunde, et al., *Nat. Struct. Biol.*, 5:31–36 (1998)), etc. The mutated intein gene is then introduced into a cell and examined for the ability to splice under permissive and non-permissive temperatures as chosen by the researcher, and can be any combination of temperatures (FIG. 11). Splicing is assayed as in Examples I through III as long as the chromosomal or intein minus extein gene is not similarly temperature sensitive.

Figure 12:
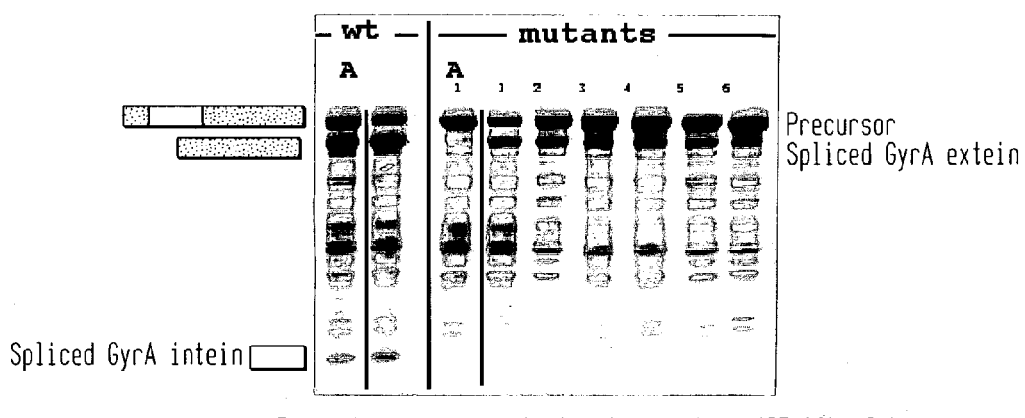
FIG. 12 show cell lysates from wild type or mutated intein clones were electrophoresed in SDS acrylamide gels. A temperature sensitive clone grown at 37° C. (labeled 'A') fails to splice, while the wild type intein clone splices (labeled 'WT'). Wild-type levels of splicing are observed in the mutant clones (1–6) when shifted to 16° C. overnight.

Using the Mxe GyrA intein in the *E.coli* GyrA extein and expressing the fusion in *E.coli* cells (Example I), we have identified several polymerase chain reaction generated mutations that render splicing of the Mxe GyrA intein temperature sensitive (FIGS. 10, 11, 12 and 13). These precursors splice at 19° C., but not at 37° C. Moreover, these mutations concentrate in the beta-sheet that includes intein Block B (FIGS. 12 and 13).

Screening for Temperature Sensitive Mxe GyrA Intein Mutants

The gyrA selection system described in Example I, can also be used to screen for temperature sensitive splicing mutants of the Mxe GyrA intein in the ofloxacin sensitive *E. coli* GyrA extein. Experiments were performed with a vector similar to pEA600. A splicing proficient clone and a splicing deficient clone (containing mutation of the intein Cys1 to Ala and Asn198 to Ala) were plated on solid media containing various concentrations of ofloxacin to determine the appropriate drug concentration to allow growth of the splicing deficient clone while blocking growth of the splicing proficient clone. The Mxe gyrA intein gene was then amplified by PCR (FIG. 10) using mutagenic strategies known to one skilled in the art and inserted into the *E. coli* gyrA gene. Libraries were plated on solid media containing ofloxacin at the predetermined concentration, replica plated and grown at either 37° C. or 16° C. (FIG. 11). Only splicing defective clones survived and grew on the plates. The replica plates were compared to identify clones that grew at 37° C., but not at 16° C. Such clones were picked and retested for temperature dependent splicing. Alternatively, the libraries of mutated Mxe GyrA inteins in *E. coli* GyrA were grown at 37° C. and then streaked onto a second plate to test for lack of growth at the splicing permissive temperature of 16° C. Splicing of the GyrA precursor was examined in clones that failed to grow at 16° C. by incubating in the absence of ofloxacin at 37° C. for 3 hours and then shifting to 16° C. overnight. Cell lysates were electrophoresed in SDS-PAGE gels that were then stained with Coomassie blue. Spliced GyrA was observed in several clones, although splicing was not complete (FIG. 12).

Figure 14:
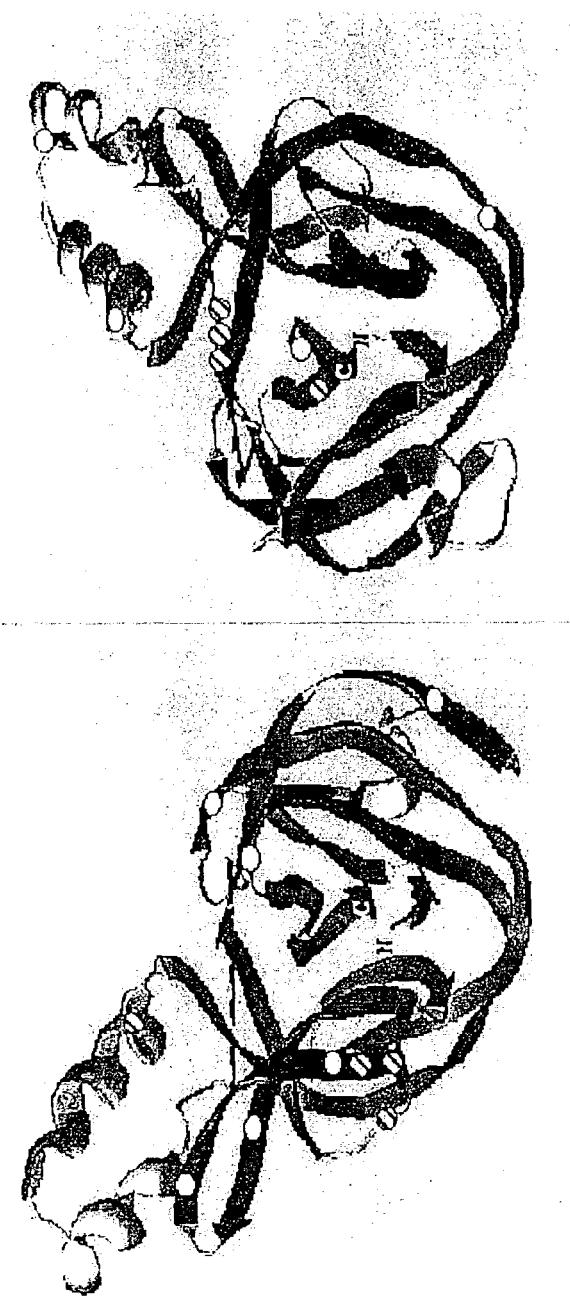
FIG. 14 illustrates the positioning of the mutations in the temperature sensitive splicing clones on the Mxe GyrA intein 3-D structure. The two panels depict opposite sides of the Mxe GyrA intein with a single Alanine preceding the intein. Double amino acid change indicates that the clone had more than one mutation.

The Mxe gyrA intein gene was sequenced from several of these temperature sensitive clones and found to have one or more mutations which are summarized in FIG. 13. The 3-D structure of the Mxe GyrA intein is known (Klabunde, et al., *Nature Struct. Biol.* 5:31–36 (1998))., GyrA enabling us to place these mutations on the Mxe GyrA intein structure (FIG. 14). We found that many of the mutations were in the beta-sheet including intein Block B (FIGS. 13 and 14), specifically in Mxe GyrA intein beta-strand B8 and the loop between beta-strands B8 and B9 (Klabunde, supra; Perler *Cell* 92:1–4 (1998)). intein Block B contains conserved intein residues thought to assist in the autocatalytic reactions at the intein N-terminal splice junction (Klabunde, supra; Noren, C. J., et al. *Angewandte Chemie* (in press)). Mutation in residues proximal in space to intein Block B, as found in this selection for temperature sensitive Mxe GyrA intein mutants, may slightly perturb the position of Block B residues, resulting in the temperature sensitive phenotype.

We suggest that mutation of the amino acids in the analogous beta-strand and loop in other inteins may generate temperature sensitive mutants of any intein. Homologous regions in other inteins can be easily identified due to the structural similarity of known intein splicing domains and intein multiple sequence alignments. To date, the 3-D structure of the Mxe GyrA intein (Klabunde, supra), the Sce VMA intein (Duan, et al., *Cell* 89:555–564 (1997)) and the Drosophila hedgehog protein autoprocessing domain (Hall, et al. *Cell*, 91:85–97 (1997)) have been determined. The splicing domain of both inteins and the N-terminal part of the hedgehog autoprocessing domain have the same protein fold; the alpha carbon trace of most of the amino acids in each of these 3 structures are superimpossible (Klabunde, supra; Perler, supra (1998)). Intein amino acid sequence similarity comparisons have also been described in the literature (Perler supra (1997), Pietrokovski, supra(1994), Pietrokovski, *Protein Sci.* 7:64–71 (1998), Dalgaard, et al., *J. Comp. Biol.* 4:193–214 (1997)).

Given the similarity in intein splicing domain structure and sequence, one skilled in the art should easily be able to identify regions in any intein that are analogous to the Mxe GyrA intein beta-strand B8 and the loop between beta-strands B8 and B9, and using this information, mutate this region to specifically generate temperature sensitive protein splicing mutants.

What is claimed is:

1. A method of detecting a temperature-sensitive intein, the method comprising:
   (a) expressing in a host cell, a precursor protein comprising a cytotoxic protein lethal to the host cell and a mutagenized intein;
   (b) selecting a host cell and culturing the host cell at a plurality of temperatures wherein splicing of the precursor protein is permitted at a first temperature and not at a second temperature and splicing results in formation of the cytotoxic protein lethal to the host cell; and
   (c) detecting the temperature-sensitive intein according to the viability of the cells at the second temperatures, whereby a temperature-sensitive intein is detected.

2. A method of detecting a temperature-sensitive intein, the method comprising:
   (a) expressing in a host cell, a precursor protein comprising a protein essential for viability of a host cell and a mutagenized intein;
   (b) selecting a host cell and culturing the host cell at a plurality of temperatures wherein splicing of the precursor protein is permitted at a first temperature and not at a second temperature and splicing results in formation of the protein essential for viability of the host cell; and
   (c) detecting the temperature-sensitive intein according to the viability of the cell at the second temperatures, whereby a temperature-sensitive intein is detected.

3. A method of detecting a temperature-sensitive intein, the method comprising:
   (a) expressing in a host cell, a precursor protein comprising a reporter protein providing a detectable phenotype and a mutagenized intein;
   (b) selecting a host cell and culturing the host cell at a plurality of temperatures wherein splicing of the precursor protein is permitted at a first temperature and not at a second temperature, and splicing results in formation of the reporter protein providing the detectable phenotype; and
   (c) detecting the temperature-sensitive intein according to the absence of the phenotype at the second temperature, whereby a temperature-sensitive intein is detected.

4. A method of detecting a temperature-sensitive intein, the method comprising:
   (a) expressing in a host cell, a precursor protein comprising a target protein detectable by size analysis and a mutagenized intein;
   (b) selecting a host cell and culturing the host cell at a plurality of temperatures wherein splicing of the precursor protein is permitted at one temperature and not at another temperature and splicing results in formation of the spliced target protein detectable by size analysis; and
   (c) detecting the temperature-sensitive intein according to the presence or absence of the spliced target protein, or the temperature sensitive intein, or both, at one temperature but not another temperature, whereby a temperature-sensitive intein is detected.

5. A negative selection system for detecting a temperature-sensitive intein, the system comprising
   a) a host cell expressing a precursor protein comprising a cytotoxic protein lethal to the host cell and a mutagenized intein;
   (b) a means of applying a plurality of temperatures suitable for permitting or inhibiting splicing of the precursor protein such that splicing results in formation of the cytotoxic protein lethal to the host cell; and
   (c) detection means for determining the viability of the host cell and determining the presence or absence of the temperature-sensitive intein.

6. A positive selection system for detecting a temperature-sensitive intein, the system comprising:
   (a) a host cell expressing a precursor protein comprising a protein essential for the viability of the host cell and a mutagenized intein;
   (b) a means of applying a plurality of temperatures suitable for permitting or inhibiting splicing of the precursor protein such that splicing results in formation of the protein essential for the viability of the host cell; and
   c) detection means for determining the viability of the host cell and determining the presence or absence of the temperature-sensitive intein.

7. A positive selection system for detecting a temperature-sensitive intein, the system comprising:
   (a) a host cell expressing a precursor protein comprising a reporter protein providing a detectable phenotype and a mutagenized intein; (b) a means of applying a plurality of temperatures suitable for permitting or inhibiting splicing of the precursor protein such that splicing results in formation of the reporter protein providing the detectable phenotype; and (c) detection means for determining the host cell phenotype and determining the presence or absence of the temperature-sensitive intein.

8. A positive selection system for detecting a temperature-sensitive intein, the system comprising:
   (a) a host cell expressing a precursor protein comprising a target protein detectable by size analysis and a mutagenized intein;
   (b) a means of applying a plurality of temperatures suitable for permitting or inhibiting splicing of the precursor protein such that splicing results in formation of the target protein; and
   (c) detection means for determining the size of the spliced products and determining the presence or absence of the temperature sensitive intein.

* * * * *

SEQUENCE LISTING

<160> NUMBER OF SEQ ID NOS: 46

<210> SEQ ID NO 1
<211> LENGTH: 186
<212> TYPE: PRT
<213> ORGANISM: Escherichia coli Gyrase A

<400> SEQUENCE: 1

Met Ser Asp Leu Ala Arg Glu Ile Thr Pro Val Asn Ile Glu Glu Glu
1               5                   10                  15

Leu Lys Ser Ser Tyr Leu Asp Tyr Ala Met Ser Val Ile Val Gly Arg
            20                  25                  30

Ala Leu Pro Asp Val Arg Asp Gly Leu Lys Pro Val His Arg Arg Val
        35                  40                  45

Leu Tyr Ala Met Asn Val Leu Gly Asn Asp Trp Asn Lys Ala Tyr Lys
    50                  55                  60

Lys Ser Ala Arg Val Val Gly Asp Val Ile Gly Lys Tyr His Pro His
65                  70                  75                  80

Gly Asp Ser Ala Val Tyr Asp Thr Ile Val Arg Met Ala Gln Pro Phe
                85                  90                  95

Ser Leu Arg Tyr Met Leu Val Asp Gly Gln Gly Asn Phe Gly Ser Ile
            100                 105                 110

Asp Gly Asp Ser Ala Ala Ala Met Arg Tyr Thr Glu Ile Arg Leu Ala
        115                 120                 125

Lys Ile Ala His Glu Leu Met Ala Asp Leu Glu Lys Glu Thr Val Asp
    130                 135                 140

Phe Val Asp Asn Tyr Asp Gly Thr Glu Lys Ile Pro Asp Val Met Pro
145                 150                 155                 160

Thr Lys Ile Pro Asn Leu Leu Val Asn Gly Ser Ser Gly Ile Ala Val
                165                 170                 175

Gly Met Ala Thr Asn Ile Pro Pro His Asn
            180                 185

<210> SEQ ID NO 2
<211> LENGTH: 127
<212> TYPE: PRT
<213> ORGANISM: Partial Mycobacterium xenopi GyrA

<400> SEQUENCE: 2

Asp Arg Ser His Ala Lys Ser Ala Arg Ser Val Ala Glu Thr Met Gly
1               5                   10                  15

Asn Tyr His Pro His Gly Asp Ala Ser Ile Tyr Asp Thr Leu Val Arg
            20                  25                  30

Met Ala Gln Pro Trp Ser Met Arg Tyr Pro Leu Val Asp Gly Gln Gly
        35                  40                  45

Asn Phe Gly Ser Pro Gly Asn Asp Pro Pro Ala Ala Met Arg Tyr Thr
    50                  55                  60

Glu Ala Pro Leu Thr Pro Leu Ala Met Glu Met Leu Arg Glu Ile Asp
65                  70                  75                  80

Glu Glu Thr Val Asp Phe Ile Pro Asn Tyr Asp Gly Arg Val Gln Glu
                85                  90                  95

Pro Thr Val Leu Pro Ser Arg Phe Pro Asn Leu Leu Ala Asn Gly Ser
            100                 105                 110

Gly Gly Ile Ala Val Gly Met Ala Thr Asn Ile Pro Pro His Asn
        115                 120                 125

<210> SEQ ID NO 3
<211> LENGTH: 438
<212> TYPE: PRT
<213> ORGANISM: Escherichia coli DnaB

<400> SEQUENCE: 3

```
Pro Pro His Ser Ile Glu Ala Glu Gln Ser Val Leu Gly Gly Leu Met
  1               5                  10                  15

Leu Asp Asn Glu Arg Trp Asp Val Ala Glu Arg Val Val Ala Asp
                 20                  25                  30

Asp Phe Tyr Thr Arg Pro His Arg His Ile Phe Thr Glu Met Ala Arg
             35                  40                  45

Leu Gln Glu Ser Gly Ser Pro Ile Asp Leu Ile Thr Leu Ala Glu Ser
         50                  55                  60

Leu Glu Arg Gln Gly Gln Leu Asp Ser Val Gly Gly Phe Ala Tyr Leu
 65                  70                  75                  80

Ala Glu Leu Ser Lys Asn Thr Pro Ser Ala Ala Asn Ile Ser Ala Tyr
                 85                  90                  95

Ala Asp Ile Val Arg Glu Arg Ala Val Val Arg Glu Met Ile Ser Val
                100                 105                 110

Ala Asn Glu Ile Ala Glu Ala Gly Phe Asp Pro Gln Gly Arg Thr Ser
            115                 120                 125

Glu Asp Leu Leu Asp Leu Ala Glu Ser Arg Val Phe Lys Ile Ala Glu
130                 135                 140

Ser Arg Ala Asn Lys Asp Glu Gly Pro Lys Asn Ile Ala Asp Val Leu
145                 150                 155                 160

Asp Ala Thr Val Ala Arg Ile Glu Gln Leu Phe Gln Gln Pro His Asp
                165                 170                 175

Gly Val Thr Gly Val Asn Thr Gly Tyr Asp Asp Leu Asn Lys Lys Thr
            180                 185                 190

Ala Gly Leu Gln Pro Ser Asp Leu Ile Ile Val Ala Ala Arg Pro Ser
        195                 200                 205

Met Gly Lys Thr Thr Phe Ala Met Asn Leu Val Glu Asn Ala Ala Met
    210                 215                 220

Leu Gln Asp Lys Pro Val Leu Ile Phe Ser Leu Glu Met Pro Ser Glu
225                 230                 235                 240

Gln Ile Met Met Arg Ser Leu Ala Ser Leu Ser Arg Val Asp Gln Thr
                245                 250                 255

Lys Ile Arg Thr Gly Gln Leu Asp Asp Glu Asp Trp Ala Arg Ile Ser
            260                 265                 270

Gly Thr Met Gly Ile Leu Leu Glu Lys Arg Asn Ile Tyr Ile Asp Asp
        275                 280                 285

Ser Ser Gly Leu Thr Pro Thr Glu Val Arg Ser Arg Ala Arg Arg Ile
    290                 295                 300

Ala Arg Glu His Gly Gly Ile Gly Leu Ile Met Ile Asp Tyr Leu Gln
305                 310                 315                 320

Leu Met Arg Val Pro Ala Leu Ser Asp Asn Arg Thr Leu Glu Ile Ala
                325                 330                 335

Glu Ile Ser Arg Ser Leu Lys Ala Leu Ala Lys Glu Leu Asn Val Pro
            340                 345                 350

Val Val Ala Leu Ser Gln Leu Asn Arg Ser Leu Glu Gln Arg Ala Asp
        355                 360                 365

Lys Arg Pro Val Asn Ser Asp Leu Arg Glu Ser Gly Ser Ile Glu Gln
```

-continued

```
    370                 375                 380

Asp Ala Asp Leu Ile Met Phe Ile Tyr Arg Asp Glu Val Tyr His Glu
385                 390                 395                 400

Asn Ser Asp Leu Lys Gly Ile Ala Glu Ile Ile Gly Lys Gln Arg
                405                 410                 415

Asn Gly Pro Ile Gly Thr Val Arg Leu Thr Phe Asn Gly Gln Trp Ser
            420                 425                 430

Arg Phe Asp Asn Tyr Ala
        435

<210> SEQ ID NO 4
<211> LENGTH: 434
<212> TYPE: PRT
<213> ORGANISM: Partial Mycobacterium tuberculosis DnaB

<400> SEQUENCE: 4

Pro Pro Gln Asp Leu Ala Ala Glu Gln Ser Val Leu Gly Gly Met Leu
  1               5                  10                  15

Leu Ser Lys Asp Ala Ile Ala Asp Val Leu Glu Arg Leu Arg Pro Gly
             20                  25                  30

Asp Phe Tyr Arg Pro Ala His Gln Asn Val Tyr Asp Ala Ile Leu Asp
         35                  40                  45

Leu Tyr Gly Arg Gly Glu Pro Ala Asp Ala Val Thr Val Ala Ala Glu
     50                  55                  60

Leu Asp Arg Arg Gly Leu Leu Arg Arg Ile Gly Gly Ala Pro Tyr Leu
 65                  70                  75                  80

His Thr Leu Ile Ser Thr Val Pro Thr Ala Ala Asn Ala Gly Tyr Tyr
                 85                  90                  95

Ala Ser Ile Val Ala Glu Lys Ala Leu Leu Arg Arg Leu Val Glu Ala
            100                 105                 110

Gly Thr Arg Val Val Gln Tyr Gly Tyr Ala Gly Ala Glu Gly Ala Asp
        115                 120                 125

Val Ala Glu Val Val Asp Arg Ala Gln Ala Glu Ile Tyr Asp Val Ala
    130                 135                 140

Asp Arg Arg Leu Ser Glu Asp Phe Val Ala Leu Glu Asp Leu Leu Gln
145                 150                 155                 160

Pro Thr Met Asp Glu Ile Asp Ala Ile Ala Ser Ser Gly Gly Leu Ala
                165                 170                 175

Arg Gly Val Ala Thr Gly Phe Thr Glu Leu Asp Glu Val Thr Asn Gly
            180                 185                 190

Leu His Pro Gly Gln Met Val Ile Val Ala Ala Arg Pro Gly Val Gly
        195                 200                 205

Lys Ser Thr Leu Gly Leu Asp Phe Met Arg Ser Cys Ser Ile Arg His
    210                 215                 220

Arg Met Ala Ser Val Ile Phe Ser Leu Glu Met Ser Lys Ser Glu Ile
225                 230                 235                 240

Val Met Arg Leu Leu Ser Ala Glu Ala Lys Ile Lys Leu Ser Asp Met
                245                 250                 255

Arg Ser Gly Arg Met Ser Asp Asp Asp Trp Thr Arg Leu Ala Arg Arg
            260                 265                 270

Met Ser Glu Ile Ser Glu Ala Pro Leu Phe Ile Asp Asp Ser Pro Asn
        275                 280                 285

Leu Thr Met Met Glu Ile Arg Ala Lys Ala Arg Arg Leu Arg Gln Lys
    290                 295                 300
```

-continued

```
Ala Asn Leu Lys Leu Ile Val Val Asp Tyr Leu Gln Leu Met Thr Ser
305                 310                 315                 320

Gly Lys Lys Tyr Glu Ser Arg Gln Val Glu Val Ser Glu Phe Ser Arg
            325                 330                 335

His Leu Lys Leu Leu Ala Lys Glu Leu Glu Val Pro Val Val Ala Ile
        340                 345                 350

Ser Gln Leu Asn Arg Gly Pro Glu Gln Arg Thr Asp Lys Lys Pro Met
            355                 360                 365

Leu Ala Asp Leu Arg Glu Ser Gly Ser Leu Glu Gln Asp Ala Asp Val
        370                 375                 380

Val Ile Leu Leu His Arg Pro Asp Ala Phe Asp Arg Asp Asp Pro Arg
385                 390                 395                 400

Gly Gly Glu Ala Asp Phe Ile Leu Ala Lys His Arg Asn Gly Pro Thr
                405                 410                 415

Lys Thr Val Thr Val Ala His Gln Leu His Leu Ser Arg Phe Ala Asn
            420                 425                 430

Met Ala

<210> SEQ ID NO 5
<211> LENGTH: 7
<212> TYPE: PRT
<213> ORGANISM: Mycobacterium tuberculosis DnaB

<400> SEQUENCE: 5

Thr Val Gln Ser Thr Lys Arg
 1               5

<210> SEQ ID NO 6
<211> LENGTH: 7
<212> TYPE: PRT
<213> ORGANISM: Mycobacterium tuberculosis DnaB

<400> SEQUENCE: 6

Arg Pro Ala Pro Arg Pro Leu
 1               5

<210> SEQ ID NO 7
<211> LENGTH: 7
<212> TYPE: PRT
<213> ORGANISM: Mycobacterium tuberculosis DnaB

<400> SEQUENCE: 7

Pro Thr Ala Arg Thr Tyr Glu
 1               5

<210> SEQ ID NO 8
<211> LENGTH: 12
<212> TYPE: PRT
<213> ORGANISM: Mycobacterium tuberculosis DnaB

<400> SEQUENCE: 8

Pro Thr Arg Pro Thr Ala Pro Pro Leu Asn Phe Ser
 1               5                  10

<210> SEQ ID NO 9
<211> LENGTH: 12
<212> TYPE: PRT
<213> ORGANISM: Mycobacterium tuberculosis DnaB

<400> SEQUENCE: 9

His Pro Asn Pro His Pro Thr Leu Ser Gly Gln Arg
```

-continued

```
                1               5                       10
```

<210> SEQ ID NO 10
<211> LENGTH: 7
<212> TYPE: PRT
<213> ORGANISM: Mycobacterium tuberculosis DnaB

<400> SEQUENCE: 10

```
Asp Leu Pro Met Val Glu Glu
  1               5
```

<210> SEQ ID NO 11
<211> LENGTH: 198
<212> TYPE: PRT
<213> ORGANISM: Mycobacterium xenopi Gyrase A intein

<400> SEQUENCE: 11

```
Cys Ile Thr Gly Asp Ala Leu Val Ala Leu Pro Glu Gly Glu Ser Val
  1               5                  10                  15

Arg Ile Ala Asp Ile Val Pro Gly Ala Arg Pro Asn Ser Asp Asn Ala
             20                  25                  30

Ile Asp Leu Lys Val Leu Asp Arg His Gly Asn Pro Val Leu Ala Asp
         35                  40                  45

Arg Leu Phe His Ser Gly Glu His Pro Val Tyr Thr Val Arg Thr Val
     50                  55                  60

Glu Gly Leu Arg Val Thr Gly Thr Ala Asn His Pro Leu Leu Cys Leu
 65                  70                  75                  80

Val Asp Val Ala Gly Val Pro Thr Leu Leu Trp Lys Leu Ile Asp Glu
                 85                  90                  95

Ile Lys Pro Gly Asp Tyr Ala Val Ile Gln Arg Ser Ala Phe Ser Val
            100                 105                 110

Asp Cys Ala Gly Phe Ala Arg Gly Lys Pro Glu Phe Ala Pro Thr Thr
        115                 120                 125

Tyr Thr Val Gly Val Pro Gly Leu Val Arg Phe Leu Glu Ala His His
    130                 135                 140

Arg Asp Pro Asp Ala Gln Ala Ile Ala Asp Glu Leu Thr Asp Gly Arg
145                 150                 155                 160

Phe Tyr Tyr Ala Lys Val Ala Ser Val Thr Asp Ala Gly Val Gln Pro
                165                 170                 175

Val Tyr Ser Leu Arg Val Asp Thr Ala Asp His Ala Phe Ile Thr Asn
            180                 185                 190

Gly Phe Val Ser His Asn
        195
```

<210> SEQ ID NO 12
<211> LENGTH: 85
<212> TYPE: PRT
<213> ORGANISM: Gallus gallus alpha-spectrin fragment

<400> SEQUENCE: 12

```
Met Arg Asn Thr Thr Gly Val Thr Glu Glu Ala Leu Lys Glu Phe Ser
  1               5                  10                  15

Met Met Phe Lys His Phe Asp Lys Asp Lys Ser Gly Arg Leu Asn His
             20                  25                  30

Gln Glu Phe Lys Ser Cys Leu Arg Ser Leu Gly Tyr Asp Leu Pro Met
         35                  40                  45

Val Glu Glu Gly Glu Pro Asp Pro Glu Phe Glu Ser Ile Leu Asp Thr
     50                  55                  60
```

-continued

Val Asp Pro Asn Arg Asp Gly His Val Ser Leu Gln Glu Tyr Met Ala
 65                  70                  75                  80

Phe Met Ile Ser Arg
                 85

<210> SEQ ID NO 13
<211> LENGTH: 416
<212> TYPE: PRT
<213> ORGANISM: Mycobacterium tuberculosis DnaB intein

<400> SEQUENCE: 13

Cys Leu Thr Ala Ser Thr Arg Ile Leu Arg Ala Asp Thr Gly Ala Glu
  1               5                  10                  15

Val Ala Phe Gly Glu Leu Met Arg Ser Gly Glu Arg Pro Met Val Trp
                 20                  25                  30

Ser Leu Asp Glu Arg Leu Arg Met Val Ala Arg Pro Met Ile Asn Val
                 35                  40                  45

Phe Pro Ser Gly Arg Lys Glu Val Phe Arg Leu Arg Leu Ala Ser Gly
     50                  55                  60

Arg Glu Val Glu Ala Thr Gly Ser His Pro Phe Met Lys Phe Glu Gly
 65                  70                  75                  80

Trp Thr Pro Leu Ala Gln Leu Lys Val Gly Asp Arg Ile Ala Ala Pro
                 85                  90                  95

Arg Arg Val Pro Glu Pro Ile Asp Thr Gln Arg Met Pro Glu Ser Glu
                100                 105                 110

Leu Ile Ser Leu Ala Arg Met Ile Gly Asp Gly Ser Cys Leu Lys Asn
                115                 120                 125

Gln Pro Ile Arg Tyr Glu Pro Val Asp Glu Ala Asn Leu Ala Ala Val
    130                 135                 140

Thr Val Ser Ala Ala His Ser Asp Arg Ala Ala Ile Arg Asp Asp Tyr
145                 150                 155                 160

Leu Ala Ala Arg Val Pro Ser Leu Arg Pro Ala Arg Gln Arg Leu Pro
                165                 170                 175

Arg Gly Arg Cys Thr Pro Ile Ala Ala Trp Leu Ala Gly Leu Gly Leu
                180                 185                 190

Phe Thr Lys Arg Ser His Glu Lys Cys Val Pro Glu Ala Val Phe Arg
    195                 200                 205

Ala Pro Asn Asp Gln Val Ala Leu Phe Leu Arg His Leu Trp Ser Ala
210                 215                 220

Gly Gly Ser Val Arg Trp Asp Pro Thr Asn Gly Gln Gly Arg Val Tyr
225                 230                 235                 240

Tyr Gly Ser Thr Ser Arg Arg Leu Ile Asp Asp Val Ala Gln Leu Leu
                245                 250                 255

Leu Arg Val Gly Ile Phe Ser Trp Ile Thr His Ala Pro Lys Leu Gly
                260                 265                 270

Gly His Asp Ser Trp Arg Leu His Ile His Gly Ala Lys Asp Gln Val
    275                 280                 285

Arg Phe Leu Arg His Val Gly Val His Gly Ala Glu Ala Val Ala Ala
    290                 295                 300

Gln Glu Met Leu Arg Gln Leu Lys Gly Pro Val Arg Asn Pro Asn Leu
305                 310                 315                 320

Asp Ser Ala Pro Lys Lys Val Trp Ala Gln Val Arg Asn Arg Leu Ser
                325                 330                 335

Ala Lys Gln Met Met Asp Ile Gln Leu His Glu Pro Thr Met Trp Lys

-continued

```
                340                345                350
His Ser Pro Ser Arg Ser Arg Pro His Arg Ala Glu Ala Arg Ile Glu
            355                360                365

Asp Arg Ala Ile His Glu Leu Ala Arg Gly Asp Ala Tyr Trp Asp Thr
    370                375                380

Val Val Glu Ile Thr Ser Ile Gly Asp Gln His Val Phe Asp Gly Thr
385                390                395                400

Val Ser Gly Thr His Asn Phe Val Ala Asn Gly Ile Ser Leu His Asn
                405                410                415
```

<210> SEQ ID NO 14
<211> LENGTH: 8
<212> TYPE: PRT
<213> ORGANISM: Mycobacterium xenopi Gyrase A

<400> SEQUENCE: 14

```
Asp Ser Ala Ala Ala Met Arg Tyr
  1               5
```

<210> SEQ ID NO 15
<211> LENGTH: 31
<212> TYPE: DNA
<213> ORGANISM: Escherichia coli Gyrase A

<400> SEQUENCE: 15
gataggctag cgatgagcga ccttgcgaga g                                31

<210> SEQ ID NO 16
<211> LENGTH: 32
<212> TYPE: DNA
<213> ORGANISM: Escherichia coli Gyrase A

<400> SEQUENCE: 16
tgaagcaatt gaattattct tcttctggct cg                               32

<210> SEQ ID NO 17
<211> LENGTH: 32
<212> TYPE: DNA
<213> ORGANISM: Nocardia otitidis-caviarum

<400> SEQUENCE: 17
cggcgactct gcggccgcaa tgcgttatac gg                               32

<210> SEQ ID NO 18
<211> LENGTH: 32
<212> TYPE: DNA
<213> ORGANISM: Nocardia otitidis-caviarum

<400> SEQUENCE: 18
ccgtataacg cattgcggcc gcagagtcgc cg                               32

<210> SEQ ID NO 19
<211> LENGTH: 31
<212> TYPE: DNA
<213> ORGANISM: Xanthomonas badrii

<400> SEQUENCE: 19
gaactgatgg ccgctctaga aaagagacg g                                 31

<210> SEQ ID NO 20
<211> LENGTH: 31
<212> TYPE: DNA

-continued

<213> ORGANISM: Xanthomonas badrii

<400> SEQUENCE: 20
ccgtctcttt ttctagagcg gccatcagtt c                                       31

<210> SEQ ID NO 21
<211> LENGTH: 61
<212> TYPE: DNA
<213> ORGANISM: Bacillus lentus

<400> SEQUENCE: 21
ggccgcaatg cgttatacgg aaatccgctt agcgaaaatt gcccatgaac tgatggccga       60
t                                                                       61

<210> SEQ ID NO 22
<211> LENGTH: 60
<212> TYPE: DNA
<213> ORGANISM: Bacillus lentus

<400> SEQUENCE: 22
ctagatcggc atcagttcat gggcaatttt cgctaagcgg atttccgtat aacgcattgc       60

<210> SEQ ID NO 23
<211> LENGTH: 39
<212> TYPE: DNA
<213> ORGANISM: Mycobacterium xenopi Gyrase A

<400> SEQUENCE: 23
cgacccgcgc ggccgcaatg cgttattgca tcacgggag                              39

<210> SEQ ID NO 24
<211> LENGTH: 45
<212> TYPE: DNA
<213> ORGANISM: Mycobacterium xenopi

<400> SEQUENCE: 24
gccaaaggcg ctaagcggat ttccgtgttg tggctgacga acccg                       45

<210> SEQ ID NO 25
<211> LENGTH: 31
<212> TYPE: DNA
<213> ORGANISM: Streptomyces phaeochromogenes

<400> SEQUENCE: 25
atgggcatgc atatatatat aggcctgggc c                                      31

<210> SEQ ID NO 26
<211> LENGTH: 30
<212> TYPE: DNA
<213> ORGANISM: Streptomyces phaeochromogenes

<400> SEQUENCE: 26
caggcctata tatatatgca tgcccattcg                                        30

<210> SEQ ID NO 27
<211> LENGTH: 39
<212> TYPE: DNA
<213> ORGANISM: Streptomyces griseoruber

<400> SEQUENCE: 27
gtttaagtct tgcttgcgat cgcttggcta tgacctgcc                              39

<210> SEQ ID NO 28
<211> LENGTH: 38
<212> TYPE: DNA
<213> ORGANISM: Streptomyces griseoruber

<400> SEQUENCE: 28
gcctgacccc gaatttgaat cgattcttga cactgttg           38

<210> SEQ ID NO 29
<211> LENGTH: 38
<212> TYPE: DNA
<213> ORGANISM: Caryophanon latum

<400> SEQUENCE: 29
gcctgacccc gaatttgaat cgattcttga cactgttg           38

<210> SEQ ID NO 30
<211> LENGTH: 38
<212> TYPE: DNA
<213> ORGANISM: Caryophanon latum

<400> SEQUENCE: 30
caacagtgtc aagaatcgat tcaaattcgg ggtcaggc           38

<210> SEQ ID NO 31
<211> LENGTH: 34
<212> TYPE: DNA
<213> ORGANISM: Gallus gallus alpha-spectrin

<400> SEQUENCE: 31
aatggtgcat gcaaggagat ggcgcccaac agtc               34

<210> SEQ ID NO 32
<211> LENGTH: 41
<212> TYPE: DNA
<213> ORGANISM: Gallus gallus alpha-spectrin

<400> SEQUENCE: 32
gctttggcta gctttcctgt gtcacctgct gatcatgaac g       41

<210> SEQ ID NO 33
<211> LENGTH: 29
<212> TYPE: DNA
<213> ORGANISM: Proteus vulgaris

<400> SEQUENCE: 33
gcgtaaagct cgcgaccgtg ctcatatcc                     29

<210> SEQ ID NO 34
<211> LENGTH: 29
<212> TYPE: DNA
<213> ORGANISM: Proteus vulgaris

<400> SEQUENCE: 34
ggatatgagc acggtcgcga gctttacgc                     29

<210> SEQ ID NO 35
<211> LENGTH: 53
<212> TYPE: DNA
<213> ORGANISM: Gallus gallus alpha-spectrin
<220> FEATURE:
<223> OTHER INFORMATION: ((W)NN)7-12 = synthetic randon oligo
<220> FEATURE:
<223> OTHER INFORMATION: At position 38, "W" = A or T
<220> FEATURE:

<223> OTHER INFORMATION: At position 39 and 40, "N" = G, C, A or T

<400> SEQUENCE: 35
tgtcaagaat cgattcaaat tcggggtcag gctctccwnn atagccaagc gat    53

<210> SEQ ID NO 36
<211> LENGTH: 11
<212> TYPE: DNA
<213> ORGANISM: Gallus gallus alpha-spectrin

<400> SEQUENCE: 36
cgcttggcta t    11

<210> SEQ ID NO 37
<211> LENGTH: 31
<212> TYPE: DNA
<213> ORGANISM: Mycobacterium tuberculosis

<400> SEQUENCE: 37
aggtgagaat tcatggcggt cgttgatgac c    31

<210> SEQ ID NO 38
<211> LENGTH: 36
<212> TYPE: DNA
<213> ORGANISM: Mycobacterium tuberculosis

<400> SEQUENCE: 38
tatataaagc tttcatgtca ccgagccatg ttggcg    36

<210> SEQ ID NO 39
<211> LENGTH: 31
<212> TYPE: DNA
<213> ORGANISM: Mycobacterium tuberculosis

<400> SEQUENCE: 39
aggtgagaat tcatggcggt cgttgatgac c    31

<210> SEQ ID NO 40
<211> LENGTH: 33
<212> TYPE: DNA
<213> ORGANISM: Mycobacterium tuberculosis

<400> SEQUENCE: 40
tttcccacgc ccgggcacgc cgccacgatg acc    33

<210> SEQ ID NO 41
<211> LENGTH: 32
<212> TYPE: DNA
<213> ORGANISM: Acetobacter aceti

<400> SEQUENCE: 41
gccgccgatc cgcgacatcg tagatttcgg cc    32

<210> SEQ ID NO 42
<211> LENGTH: 32
<212> TYPE: DNA
<213> ORGANISM: Acetobacter aceti

<400> SEQUENCE: 42
ggccgaaatc tacgatgtcg cggatcggcg gc    32

<210> SEQ ID NO 43
<211> LENGTH: 89

```
<212> TYPE: DNA
<213> ORGANISM: Gallus gallus alpha-spectrin
<220> FEATURE:
<223> OTHER INFORMATION: ((W)NN)7-12 = synthetic randon oligo
<220> FEATURE:
<223> OTHER INFORMATION: At position 38, "W" = A or T
<220> FEATURE:
<223> OTHER INFORMATION: At position 39 and 40, "N" = A, G, C or T

<400> SEQUENCE: 43
tgtcaagaat cgattcaaat tcggggtcag gctctccwnn atagccaagc gatcgcaggc      60
agcttttaaa gccctgatgg ttcagacgt                                        89

<210> SEQ ID NO 44
<211> LENGTH: 15
<212> TYPE: DNA
<213> ORGANISM: Gallus gallus alpha-spectrin

<400> SEQUENCE: 44
ctgaaccatc agggc                                                       15

<210> SEQ ID NO 45
<211> LENGTH: 7
<212> TYPE: PRT
<213> ORGANISM: Mycobacterium xenopi Gyrase A

<400> SEQUENCE: 45

Glu Ile Arg Leu Ala Lys Ile
  1               5

<210> SEQ ID NO 46
<211> LENGTH: 199
<212> TYPE: PRT
<213> ORGANISM: Mycobacterium xenopi Gyrase A

<400> SEQUENCE: 46

Cys Ile Thr Gly Asp Ala Leu Val Ala Leu Pro Glu Gly Glu Ser Val
  1               5                  10                  15

Arg Ile Ala Asp Ile Val Pro Gly Ala Arg Pro Asn Ser Asp Asn Ala
             20                  25                  30

Ile Asp Leu Lys Val Leu Asp Arg His Gly Asn Pro Val Leu Ala Asp
         35                  40                  45

Arg Leu Phe His Ser Gly Glu His Pro Val Tyr Thr Val Arg Thr Val
     50                  55                  60

Glu Gly Leu Arg Val Thr Gly Thr Ala Asn His Pro Leu Leu Cys Leu
 65                  70                  75                  80

Val Asp Val Ala Gly Val Pro Thr Leu Leu Trp Lys Leu Ile Asp Glu
                 85                  90                  95

Ile Lys Pro Gly Asp Tyr Ala Val Ile Gln Arg Ser Ala Phe Ser Val
            100                 105                 110

Asp Cys Ala Gly Phe Ala Arg Gly Lys Pro Glu Phe Ala Pro Thr Thr
        115                 120                 125

Tyr Thr Val Gly Val Pro Gly Leu Val Arg Phe Leu Glu Ala His His
    130                 135                 140

Arg Asp Pro Asp Ala Gln Ala Ile Ala Asp Glu Leu Thr Asp Gly Arg
145                 150                 155                 160

Phe Tyr Tyr Ala Lys Val Ala Ser Val Thr Asp Ala Gly Val Gln Pro
                165                 170                 175
```

```
Val Tyr Ser Leu Arg Val Asp Thr Ala Asp His Ala Phe Ile Thr Asn
            180                 185                 190

Gly Phe Val Ser His Asn Thr
            195
```